US006610479B1

(12) United States Patent
Lundeberg et al.

(10) Patent No.: US 6,610,479 B1
(45) Date of Patent: Aug. 26, 2003

(54) ACTIVATING A REVERSIBLY INACTIVATED IMMOBILIZED ENZYME BY RELEASE FROM AN IMMOBILIZING MOIETY

(75) Inventors: Joakim Lundeberg, Stockholm (SE); Mathias Uhlén, Stockholm (SE)

(73) Assignee: Dynal AS, Oslo (NO)

( * ) Notice: Subject to any disclaimer, the term of this patent is extended or adjusted under 35 U.S.C. 154(b) by 0 days.

(21) Appl. No.: 08/952,570

(22) PCT Filed: May 9, 1996

(86) PCT No.: PCT/GB96/01108
§ 371 (c)(1),
(2), (4) Date: Feb. 13, 1998

(87) PCT Pub. No.: WO96/35779
PCT Pub. Date: Nov. 14, 1996

(30) Foreign Application Priority Data

May 9, 1995 (GB) .............................. 9509336

(51) Int. Cl.⁷ .......................... C12Q 1/68; C12P 19/34; C12N 11/16; C12N 15/00
(52) U.S. Cl. .......................... 435/6; 435/91.1; 435/174; 435/177; 435/320.1; 435/440; 435/810
(58) Field of Search .......................... 435/6, 89, 91.1, 435/174, 176, 177, 180, 440, 320.1, 810

(56) References Cited

U.S. PATENT DOCUMENTS

| | | | |
|---|---|---|---|
| 4,889,818 A | 12/1989 | Gelfand et al. | 435/194 |
| 5,190,864 A | * 3/1993 | Giese et al. | 435/41 |
| 5,338,671 A | * 8/1994 | Scalice et al. | 435/91.2 |
| 5,565,340 A | * 10/1996 | Chenchik et al. | 435/91.2 |
| 5,679,539 A | * 10/1997 | Hudson et al. | 435/68.1 |
| 5,693,517 A | * 12/1997 | Gelfand et al. | 435/193 |
| 5,871,906 A | * 2/1999 | Dyer et al. | 435/6 |

OTHER PUBLICATIONS

Nilsson Et Al., Eur. J. Biochem. 224, 103–108 (1994).*
Sharkey Et Al., Bio/Technology, vol. 12, May 1994, pp. 506–509.*
Barnes, W.M., "The fidelity of Taq polymerase catalyzing PCR is improved by an N-terminal deletion", Gene 112:29–35, 1992.
Barnes, W.M., "PCR amplification of up to 35–kb DNA with high fidelity and high yield from lambda . . . ", Proc. Acad. Natl. Sci. USA 91:2216–2220, 1994.
Cheng et al., "Effective amplification of long targets from cloned inserts and human genomic DNA", Proc. Natl. Acad. Sci. USA 91:5695–5699, 1994.
Chou et al., "Prevention of pre–PCR mis–priming and primer dimerization improves low–copy–number . . . ", Nucleic Acids Research 20:1717–1723, 1992.
Cook et al., "Transcription by an immobilized RNA polymerase from bacteriophage T7 and the topology . . . ", Nucleic Acids Research 20:3591–3598, 1992.
D'Aquila et al., "Maximizing sensitivity and specificity of PCR by pre–amplifiction heating", Nucleic Acids Research 19:3749, 1991.
Faloona et al., "Direct Detection of HIV sequences in Blood: High–gain polymerase chain reaction", Abstract 1019, Publications, p. 318.
Fujita et al., "Surprising Lability of Biotin–Streptavidin Bond During Transcription of Biotinylated . . . ", BioTechniques 14:608–617, 1993.
Kellogg et al., "TaqStart Antibody: 'Hot Start' PCR Facilitated by a Neutralizing Monoclonal Antibody . . . ", BioTechniques 16:1134–1137, 1994.
Kwok et al., "Uracil–N–Glycosylase Enhances Specificity of PCR Amplifications", Abstract D–120, Abstracts of the General Meeting, p. 116, 1992.

* cited by examiner

Primary Examiner—David M. Naff
(74) Attorney, Agent, or Firm—Fish & Richardson P.C.

(57) ABSTRACT

Enzymes or catalytic fragments thereof reversibly inactivated by attachment to an immobilizing moiety which may comprise a magnetic particle are activated by release from the immobilizing moiety. The enzyme or fragment may be in the form of a fusion protein that is attached to the immobilizing moiety via a pair of affinity binding partners such that the enzyme or fragment is reversibly inactivated, and release of the fusion protein from the immobilizing moiety activates the enzyme or fragment. Enzymes include DNA polymerases, DNA ligases, Reverse transcriptases and RNA polymerases. The enzyme or fragment may be thermostable, and the fusion protein can be bound to the immobilizing moiety via a heat-labile linkage. Activation of the reversibly inactivated immobilized enzyme or fragment has particular utility in PCR and analogous nucleic acid amplification techniques. A sample containing a nucleic acid is contacted with the immobilized fusion protein, and release of the fusion protein activates the enzyme or fragment to start a first cycle of an amplification reaction. Amplification reactions that may be carried out include Ligase chain reaction (LCR), Self-sustained Sequence Replication (3SR), Reverse transcriptase PCR (RT-PCR), Q-beta replicase amplification reaction and nucleic acid sequence-based amplification (NASBA). Kits for the amplifications may be prepared containing an appropriate reversibly immobilized enzyme in the form of a fusion protein, and primers and/or probe for performing the amplification.

19 Claims, 9 Drawing Sheets

ACTIVATING A REVERSIBLY INACTIVATED IMMOBILIZED ENZYME BY RELEASE FROM AN IMMOBILIZING MOIETY

This is a continuation of International Patent Application No. PCT/GB96/01108, with an International Filing Date of May 9, 1996, now pending.

FIELD OF THE INVENTION

The present invention relates to the activation of enzymes by their release from an immobilizing moiety, and in particular heat-mediated release.

BACKGROUND OF THE INVENTION

The increasing availability of enzymes from various organisms with specific defined activities has led to the use of these catalysts as reagents in many in vitro and in vivo systems. Notably, methods of detection and analysis in the area of molecular biology require the use of a least one of the enzymes involved in DNA/RNA replication, transcription and/or translation. Precise control of the activity of these enzymes is generally achieved through precise knowledge of their pH, temperature, ionic strength and cofactor requirements and the consideration of other criteria essential for their working. Not only is the ability to control activation of these enzymes important, but also the ability to inactivate the enzymes, generally reversibly. The capacity to turn the activity of an enzyme on and off is often crucial to the correct functioning of a particular analytical or diagnostic assay.

For many years a limitation of molecular biological methods was the difficulty in obtaining sufficient amounts of homogeneous DNA for further analysis. This problem was largely overcome by the development of the Polymerase chain reaction (PCR) method which has, since its inception in the late 1980s, been responsible for many of the advancements in the genetic engineering field. A number of related amplification techniques employing the same principle as PCR have evolved from the basic concept of PCR, namely cycles of replication, denaturation and reannealing with suitable primers.

In order to obtain an amplified DNA product which is homogeneous, strict regulation of the cycles is required, in terms of time and temperature, the activity of the enzymes employed, for example the Taq polymerase, the choice of primers and the conditions of hybridization and denaturation. Thus, ideally, primers which anneal to complementary strands of target double stranded DNA are added to the DNA which has been denatured. The primers are then annealed under suitable conditions of stringency to prevent binding to non-complementary sequences. DNA extension along the length of the DNA template 3' of the annealed primer is then performed using a suitable DNA polymerase. After a desired extended product is achieved, denaturation conditions are effected to allow separation of the parent and daughter strands which may then reenter the cycle.

In the laboratory situation, temporal control of each consecutive event is not routinely performed and a reaction mix is employed in which the change of temperature during the course of the cycle is the initiator of the consecutive steps. However, reliance on such temperature control can lead to problems resulting in a heterogeneous product. For example, in experimental procedures in which a reaction mix is heated to a temperature of around 90° C. to effect denaturation, if all the components necessary for the polymerase reaction are present during the heating step, spurious annealing of the primers to non-complementary strands and subsequent extension may occur, resulting in amplification of non-target DNA. Although efficiencies of thermostable DNA polymerases are greatly reduced at ambient temperature relative to their peak efficiencies at higher temperatures, sufficient activity may be present at ambient temperatures to cause PCR side-products. Commonly, dimerized primer-amplified fragments ("primer dimer") as well as larger non-specific side-reaction products (mis-primed products) are obtained. The non-specific fragments can vary in size and yield, are primer sequence dependent and are most likely to arise from reactions using complex (e.g. genomic) DNA. Such non-specific fragments have been observed to reduce the yield of desired specific fragments through competition with the specific target in the reaction. Furthermore, non-specific products that are approximately the same size as the specific product can cause confusion when interpreting results. PCR amplifications particularly prone to generation of a variety of side reaction products include those involving one or more of the following: complex genomic DNA or cDNA templates; degenerate primers; very low-copy-number targets; large numbers of thermal cycles (i.e. >35); more than one target sequence in the same tube (i.e. multiplex PCR).

This has led to the introduction of a number of techniques for initiating the cycle at the temperature of denaturation, the so-called "hot start" method (Chou et al. (1992) Nucl. Acids Res., 20, 1717–1723; D'Aquila et al. (1991) Nucl. Acids Res., 19, 3749; Faloona et al. (1990) 6th International conference on AIDS,. San Francisco, Calif., USA, Abstract No. 1019). "Hot start" methods have found particular utility for long range PCR. For many years PCR was restricted to amplification of a few thousand bases. However, successful amplification of up to 40 kbp has been achieved using a mixture of different thermostable enzymes employing the "hot start" procedure. If the "hot start" procedure is not used in this case, comparatively short non-specific products are preferentially amplified. The "hot start" procedure is also beneficial when low-copy-number targets are to be amplified or for in situ PCR.

The original approach to achieve "hot start" of the polymerase reaction was to withhold an essential reagent of the reaction (for example the DNA polymerase, $MgCl_2$, primers, deoxyribonucleoside triphosphates and/or DNA sample) until the reaction mixture was heated to a high temperature (e.g. >55° C.), followed by the addition of the missing component. Another approach is the use of a heat-labile wax or jelly barrier that melts and permits mixing of aqueous components at an elevated temperature. However, both these "hot start" methods suffer from the drawback that they have increased probability of crossover contamination on reopening the reaction tubes and that they are cumbersome and time-consuming when working with multiple samples.

An alternative to "hot start" approaches which prevents PCR product carryover to subsequent cycles and allows the addition of all components of the PCR reaction at one time, involves the use of dUTP and the DNA repair enzyme uracil-N-glycosylase (UNG) in PCR reactions. In this method UNG digests the dU-incorporated nonspecific products before thermal cycling commences, thereby reducing the amplification of these side products in the reaction (Kwok et al. (1992) 92nd Gen. Mtg. Am. Soc. Microbiol., 116 (Abstract No. D-120). However, this method is not widely used owing to the added expense of the additional reagents and the reduced yield of specific products which may result as a consequence of using dUTP in PCR.

A "hot start" method which allows the addition of all components of the PCR reaction at one time employs an antibody marketed by Clontech Laboratories, Palo Alto, California, USA, which binds to and inactivates Taq polymerase at ambient temperatures, but releases the active DNA polymerase once the high temperatures (above 70° C.) have been obtained. However, not all antibodies are suitable for this methodology as it was found that of the IgGs derived from 12 hybridoma clones whose supernatants had affinity for Taq DNA polymerase, only the IgGs from 4 of the clones inactivated Taq polymerase in solution. The remainder although having affinity for the polymerase did not block its activity. Furthermore, this method suffers from the drawback that the active polymerase is released from the inactivating antibody at a particular temperature which cannot be manipulated to suit the particular requirements of different PCR reactions.

SUMMARY OF THE INVENTION

Surprisingly, it has now been found that enzymes may be reversibly inactivated by attachment to an immobilizing moiety, and activated by their release from said moiety. In particular, it has been found that Taq polymerase may be inactivated when immobilized, but may be activated by disruption of the association with the immobilizing moiety.

In one aspect, therefore, the present invention provides a method of activating a reversibly inactivated enzyme, wherein the enzyme is inactivated by attachment to an immobilizing moiety and is activated by release from said moiety.

Enzymes within the scope of the invention include any of the enzymes known and described in the art, but especially enzymes employed in the replication, transcription and translation of DNA or RNA. In particular such enzymes include polymerases, ligases, reverse transcriptases, replicases, exonucleases and ribozymes. Also included are enzyme entities which are functionally equivalent to native enzymes, but which have been modified by genetic or chemical manipulation, and which may have structural or sequence homology. Active fragments of enzymes may also be used. The invention has been shown to be particularly effective in the case of enzymes which move relative to their substrates during the course of the reaction they catalyze. Such "translocatable" enzymes include for example DNA polymerase enzymes which act on successive portions of the DNA template strand during the replication reaction. After immobilization the enzyme and its substrate (or other components of the catalytic reaction) are no longer able to interact appropriately. Whilst not wishing to be bound by theoretical considerations, one possible mechanism which may explain the inability of translocatable enzymes to function when immobilized is that the movement necessary for the correct functioning of such translocatable enzymes is hindered or prevented by immobilization. An alternative mechanism to explain the inactivation of enzymes on immobilization is that active sites available before immobilization are subsequently inaccessible. For example, if the immobilizing moiety is a hydrophobic solid support and hydrophobic regions make up the active site, binding between these regions may effectively remove the active site making it inaccessible to substrates.

Preferably, the enzymes have DNA polymerase, reverse transcriptase or ligase activity and especially preferably they are also thermostable.

As will be described in more detail below, the enzymes may be used in the form of a fusion protein comprising all or a portion of the enzyme fused with an additional polypeptide or peptide moiety. Fusion may be effected genetically or chemically using techniques well known in the art.

The immobilizing moiety bound to the enzyme may be any solid support which upon binding inhibits the activity of the enzyme in question to a level which is conducive to the requirements of the assay or system for which it is used. Numerous solid supports suitable as immobilizing moieties according to the invention, are well known in the art and widely described in the literature and generally speaking, the solid support may be any of the well-known supports or matrices which are currently widely used or proposed for immobilization, separation etc. in chemical or biochemical procedures. Thus for example, the immobilizing moieties may take the form of particles, sheets, gels, filters, membranes, microfibre strips, tubes or plates, fibres or capillaries, made for example of a polymeric material e.g. agarose, cellulose, alginate, teflon, latex or polystyrene. Biochips may be used as solid supports to provide miniature experimental systems as described for example in Nilsson et al. (Anal. Biochem. (1995), 224, 400–408) or as a diagnostic tool. Particulate materials, especially beads, are generally preferred. For example, Sepharose or polystyrene beads may be used. The immobilizing moiety may comprise magnetic particles, which permit the ready separation of immobilized material by magnetic aggregation. The requirement of such a moiety is that it is stable to the conditions at which release and hence activation of the enzyme moiety is needed.

It is also envisaged that it may be possible to design the immobilizing moiety such that on subjection to the "release" conditions, although not actually physically set free from the enzyme moiety, its structural configuration is altered such that the attached enzyme moiety is able to interact appropriately with its substrate and/or other essential components. The term "release" as used herein thus includes not only physical separation of the enzyme from the support but also situations where, although not physically freed from the support, the conformation of the support and/or enzyme is altered such that the enzyme may resume correct functioning. More commonly however, activation is achieved by physical separation of the enzyme from the immobilizing moiety.

The immobilizing support may carry further moieties for attachment of the enzyme. Generally speaking, these will comprise one of a pair of affinity binding partners, such as biotin and avidin or streptavidin, PNA or DNA and DNA binding protein (e.g. either the lac I repressor protein or the lac operator sequence to which it binds), antibodies (which may be mono- or polyclonal), antibody fragments or the epitopes or haptens of antibodies. In these cases, one partner of the binding pair is attached to (or is inherently part of) the immobilizing moiety and the other partner is attached to (or is inherently part of) the enzyme of interest or catalytic fragment/mutant thereof. The afore-mentioned binding moieties may be attached to the immobilizing support by methods well known in the art, which include for example, attachment-through hydroxyl, carboxyl, aldehyde or amino groups which may be provided by treating the immobilizing support to provide suitable surface coatings. U.S. Pat. No. 4,654,267 describes the introduction of many such surface coatings.

Attachment of the enzyme to the immobilizing moiety may be achieved by any reversible means which permits ready release of the enzyme at the desired conditions. Reversible as mentioned in this context indicates only that attachment of the enzyme to the support is reversible, ie. that the enzyme may be released from the support, and not that the linkage is necessarily capable of being reformed thereafter. Attachment may be, for example, via a linkage which is sensitive to heat, light, microwaves, pH, acid or proteases.

Preferably, the enzyme is attached through a heat-labile attachment which permits ready release simply by raising the temperature. In such a case, once a suitable temperature is obtained in a reaction, for example in PCR, the active enzyme is released. Such attachment may for example occur through antibody binding to an epitope of the enzyme or of an appended non-functional moiety, which is disrupted by heating. Alternatively, other heat-labile protein-protein, protein-DNA or DNA-DNA attachments may be used, wherein DNA may also be replaced by PNA. For example, biotin-streptavidin, protein A-antibody, protein G-human serum albumin (HSA) pairing may be used, with either component of the pair (or functional part thereof) being attached to, or inherently part of, the enzyme moiety. For example, a synthetic monovalent IgG-binding domain Z derived from protein A or a serum-binding region BB or ABP from protein G (which are referred to in the Examples hereinafter) may be used to bind to IgG or HSA respectively. Where applicable, for example in fusion proteins, more than one of the above mentioned Z or B domains may be employed to increase binding to a solid support bearing the other component of the pair (Nilsson et al., Eur. J. Biochem. (1994), 224, 103–108). Specific antibodies and molecules bearing the epitope to which the antibody is directed may also be used, e.g. biotin:anti-biotin antibody.

Proteins or polypeptide fragments which interact with specific DNA sequences may be employed, for example proteins containing the zinc finger motif or proteins of the lac system. Of particular use may be the use of stretches of double stranded DNA in which one strand is immobilized and the other attached to the enzyme moiety. The length and sequence/GC content of the DNA stretch may be made such that the melting temperature, Tm, may be predicted and customized to the reaction in question. Thus, in PCR for example, the temperature at which the DNA polymerase is released may be strictly controlled.

Release may also be effected indirectly by heat. For example, proteinases active only at extreme temperatures or activated at extreme temperatures may be used to cleave specific cleavage sites between the enzyme and immobilization moiety.

The above-mentioned method has particular utility in PCR and analogous nucleic acid amplification techniques. As mentioned above, there is a need for an improved method of "hot start" in nucleic acid amplification procedures, and a temperature-dependent enzyme activation method according to the present invention has particular utility in this regard.

In another aspect, the present invention thus also provides, a method of amplification of nucleic acid comprising subjecting a sample of nucleic acid to one or more cycles of in vitro amplification using an amplification enzyme, characterised in that said enzyme is provided in reversibly inactivated form attached to an immobilising moiety and is activated by release from said moiety during the first amplification cycle, whereupon the enzyme-catalyzed amplification reaction may proceed. Preferably a thermostable amplification enzyme is employed and release is effected by raising the temperature.

The generation of non-specific amplification products is thus reduced or avoided.

Any in vitro amplification method may be used, including especially PCR and its modifications.

The activation temperature necessary to achieve release of the enzyme conveniently may be the temperature to which the reaction mix is heated in the first cycle to achieve strand separation. This may be selected to suit the system and temperatures up to e.g. 90–95° C. may be used. Alternatively, lower temperatures e.g. 70–77° C. or down to 40–55° C. may be more appropriate in other systems, depending on the amplification method, enzyme, reaction conditions, nature of the nucleic acid being amplified, etc.

Modifications of the classical PCR method include, for example, the use of nested primers, in which an additional two "inner" primer are used, which "nest" or hybridise between the first "outer" primer pair. The use of four separate priming events results in increased specificity of the amplification reaction.

Other amplification techniques worthy of mention include Ligase chain reaction (LCR), Self-sustained Sequence Replication (3SR), the Q-beta replicase amplification system and the NASBA technique (see for example Abramson and Myers (1993) Current Opinion in Biotech., 4, 41–47).

LCR which may be used to both amplify DNA and discriminate a single base mutation employs four oligonucleotides, two adjacent oligonucleotides which uniquely hybridize to one strand of target DNA and a complementary set of adjacent oligonucleotides, which hybridize to the opposite strand. Thermostable DNA ligase will then covalently link each set, provided that there is complete complementarity at the junction. This concept forms the basis of the Oligonucleotide Ligation Assay (OLA) described by Landegren et al. (Science (1988), 241, 1077–1080). Because the oligonucleotide products from one round may serve as substrates during the next round, the signal is amplified exponentially, analogous to PCR amplification. A single-base mismatch at the oligonucleotide junction will not be amplified and is therefore distinguished. The use of ligases in PCR-based methods is reviewed by Barany (PCR Methods and Applications 1991, 1, 5–16).

In 3SR, primers are used which carry RNA polymerase binding sites permitting the action of reverse transcriptase to amplify target RNA or ssDNA. In a modification of this technique, referred to as Reverse transcriptase-PCR (RT-PCR) enzymes having reverse transcriptase and DNA polymerase acivities may be used such that first strand cDNA synthesis (as achieved by the activity of reverse transcriptase) may be coupled to PCR amplification by the action of the DNA polymerase. Such enzymes include for example Thermus thermophilus DNA polymerase (rTTh).

In the Q-beta replicase system, an immobilised probe captures one strand of target DNA and is then caused to hybridise with an RNA probe which carries as a template region a tertiary structure known as MDV-1 for an RNA-directed RNA polymerase, normally Q-beta replicase.

Thus, the enzyme of the invention may be a DNA polymerase, DNA ligase, reverse transcriptase or RNA polymerase attached to an immobilizing moiety, for example Sepharose beads, via a binding pair or antibody as described previously. In the PCR reaction, for example, at ambient temperature, the DNA polymerase is inactive, but on heating during the course of the first cycle of PCR the enzyme is released and concomitantly activated. When more than one enzyme is used during the amplification reaction, ie. when more than one amplification enzyme is present, one or both of said enzymes may be inactivated by immobilization. Thus for example, in one-step RT-PCR an immobilized DNA polymerase may be employed and the reverse transcription step may be performed using mesophilic reverse transcriptases. The DNA polymerase may then be activated during the first heating cycle of PCR.

In a further aspect, the invention provides reversibly inactivated enzymes attached to an immobilizing moiety, in particular DNA polymerase attached to an immobilizing moiety.

The invention also extends to kits, comprising at least the following:
a) for PCR, an immobilized, reversibly inactivated DNA polymerase and a pair of primers which hybridise to opposite strands of the target DNA;
b) for LCR, an immobilized, reversibly inactivated DNA ligase and two pairs of primers wherein the individual primers of the pairs hybridise to adjacent stretches of DNA and each pair hybridises to complementary regions of opposite strands of the target DNA;
c) for 3SR, an immobilized, reversibly inactivated reverse transcriptase and/or RNA polymerase, a pair of primers which hybridize to opposite strands of the target DNA (or corresponding RNA) and which each have a polymerase binding site;
d) for RT-PCR, an immobilized, reversibly inactivated reverse transcriptase with DNA polymerase activity, a primer which hybridizes to the target RNA and a pair of primers which hybridize to opposite strands of the target CDNA once formed;
e) for Q-beta replicase amplification, an immobilized, reversibly inactivated RNA-directed RNA polymerase, a DNA primer and an RNA probe with a 5'-MDV-1 structure, the capture oligonucleotide being immobilised or permitting immobilisation.

In all the above kits, nucleotide bases will normally be supplied together with appropriate buffers.

Figure 7:
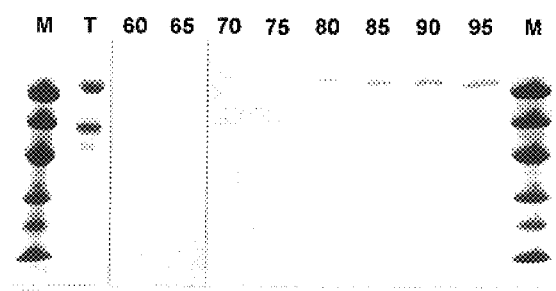
Figure 3:
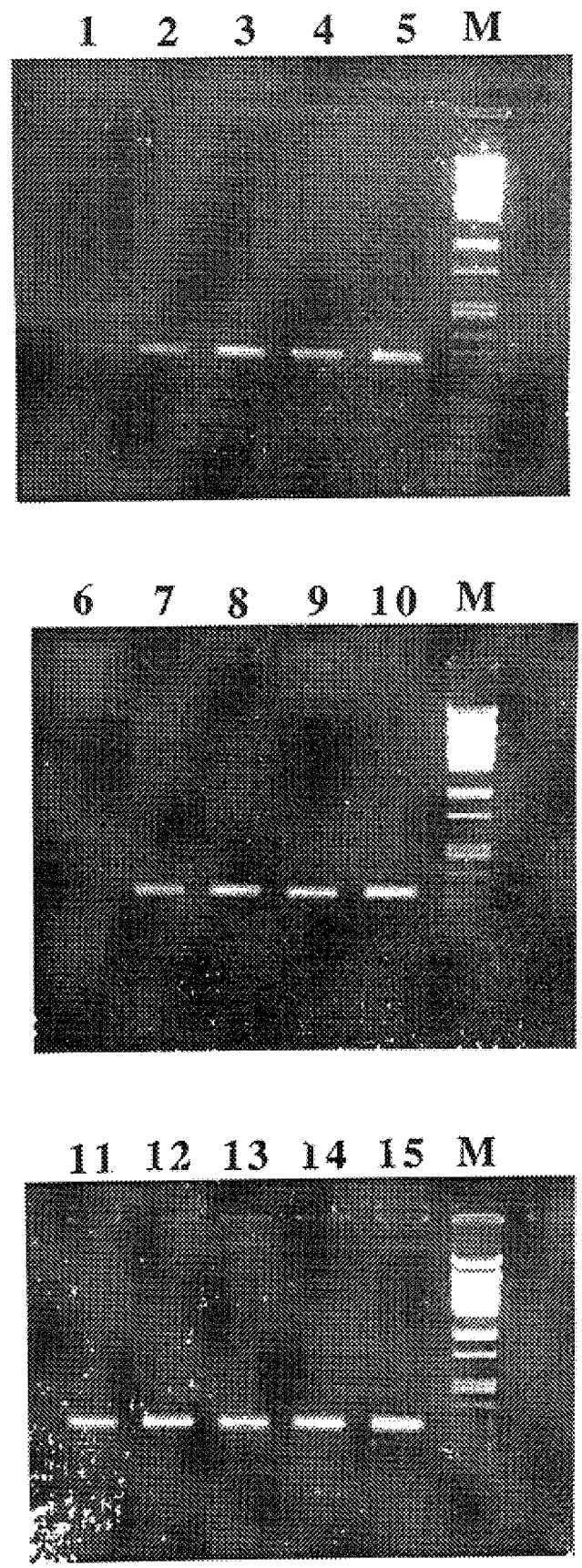
Figure 4:
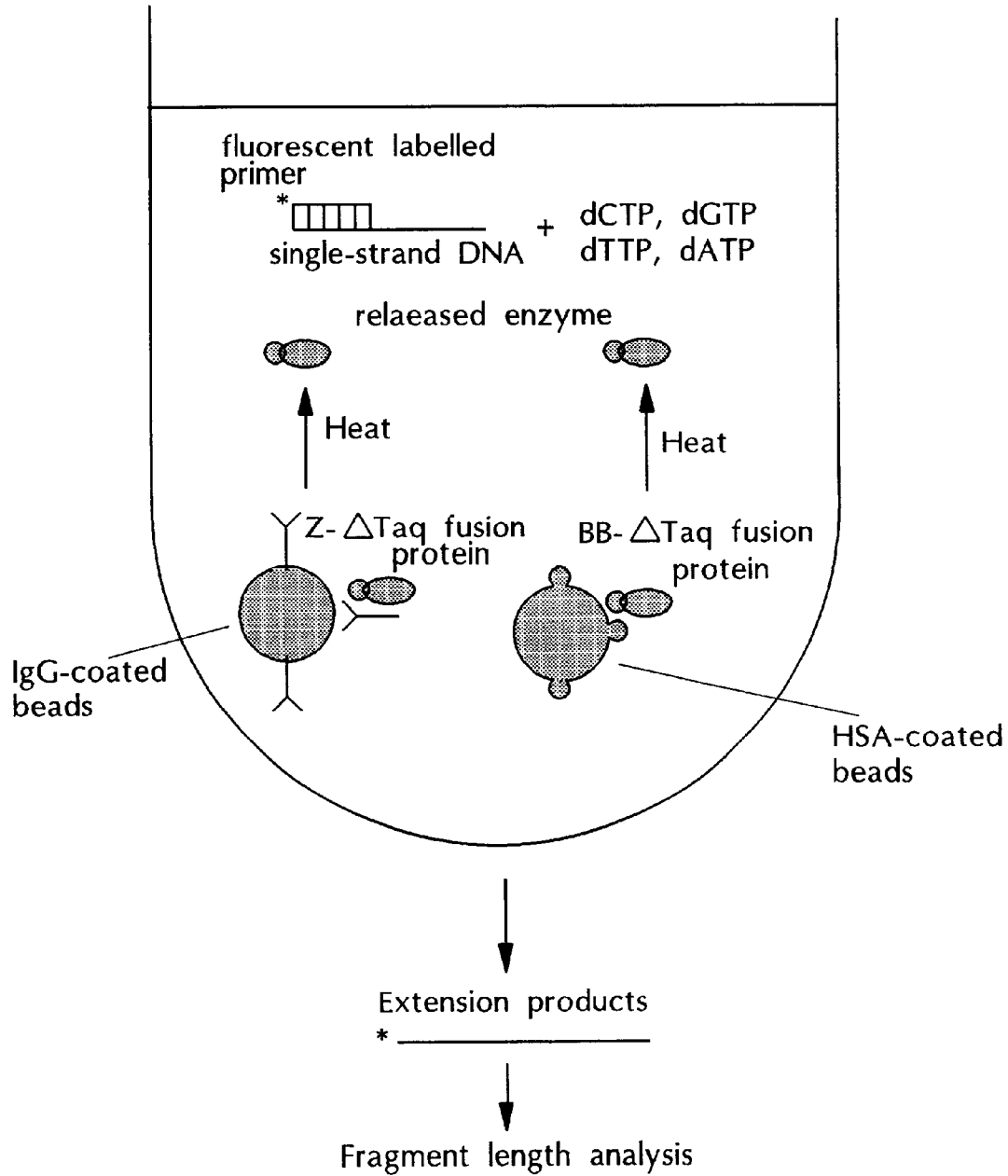
Figure 5:
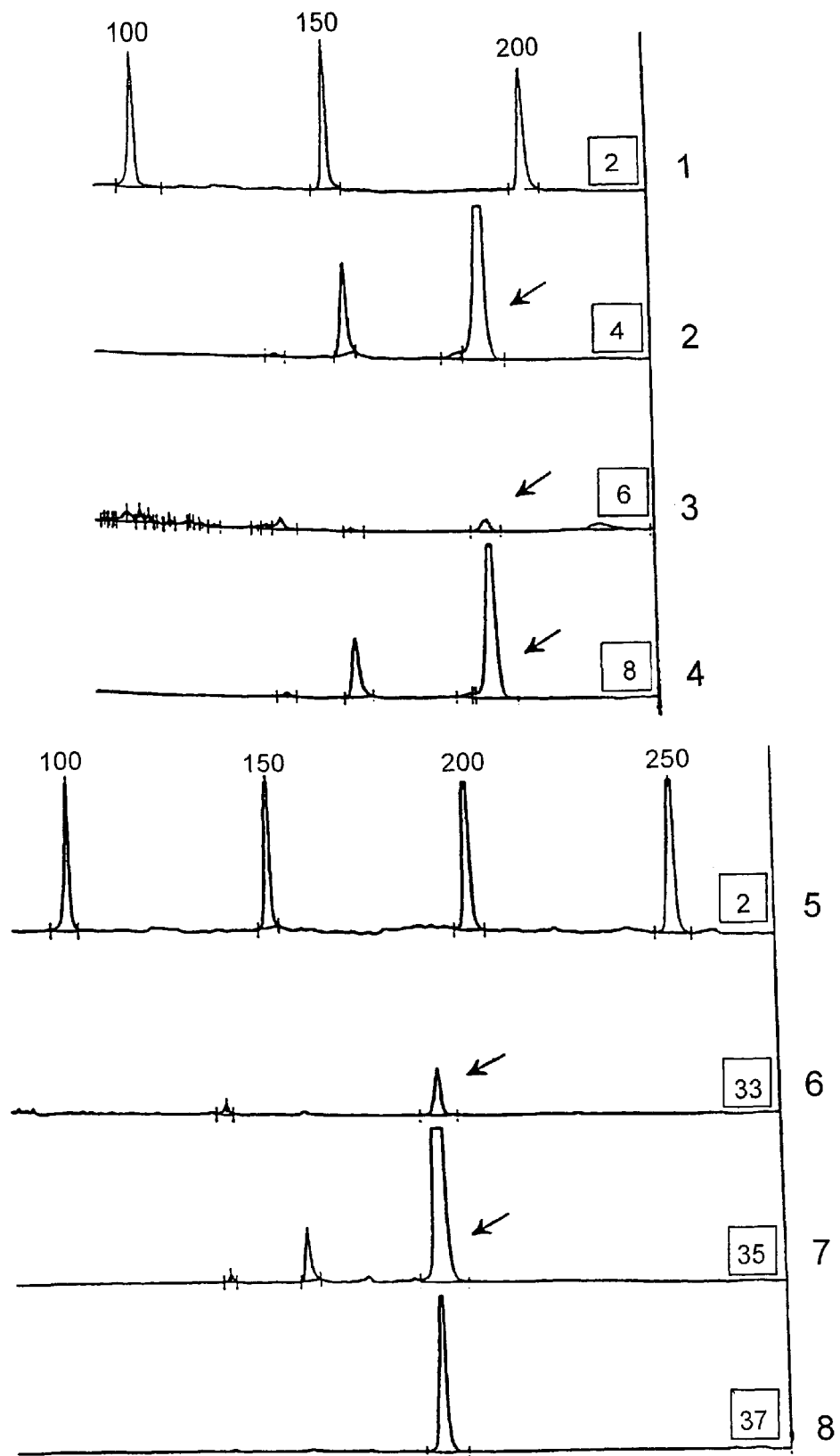
Figure 6:
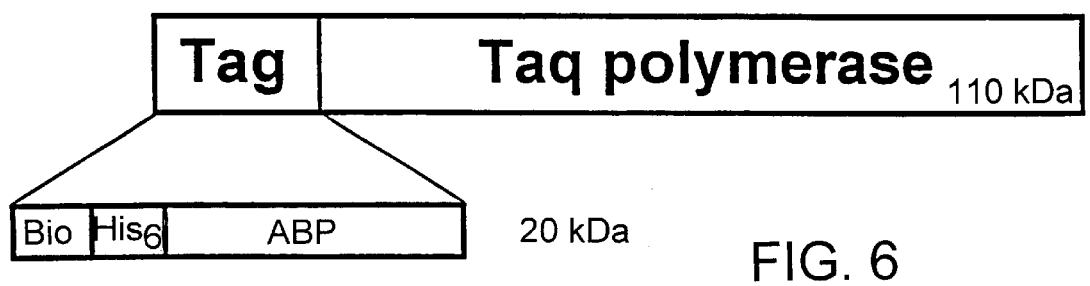
Figure 8:
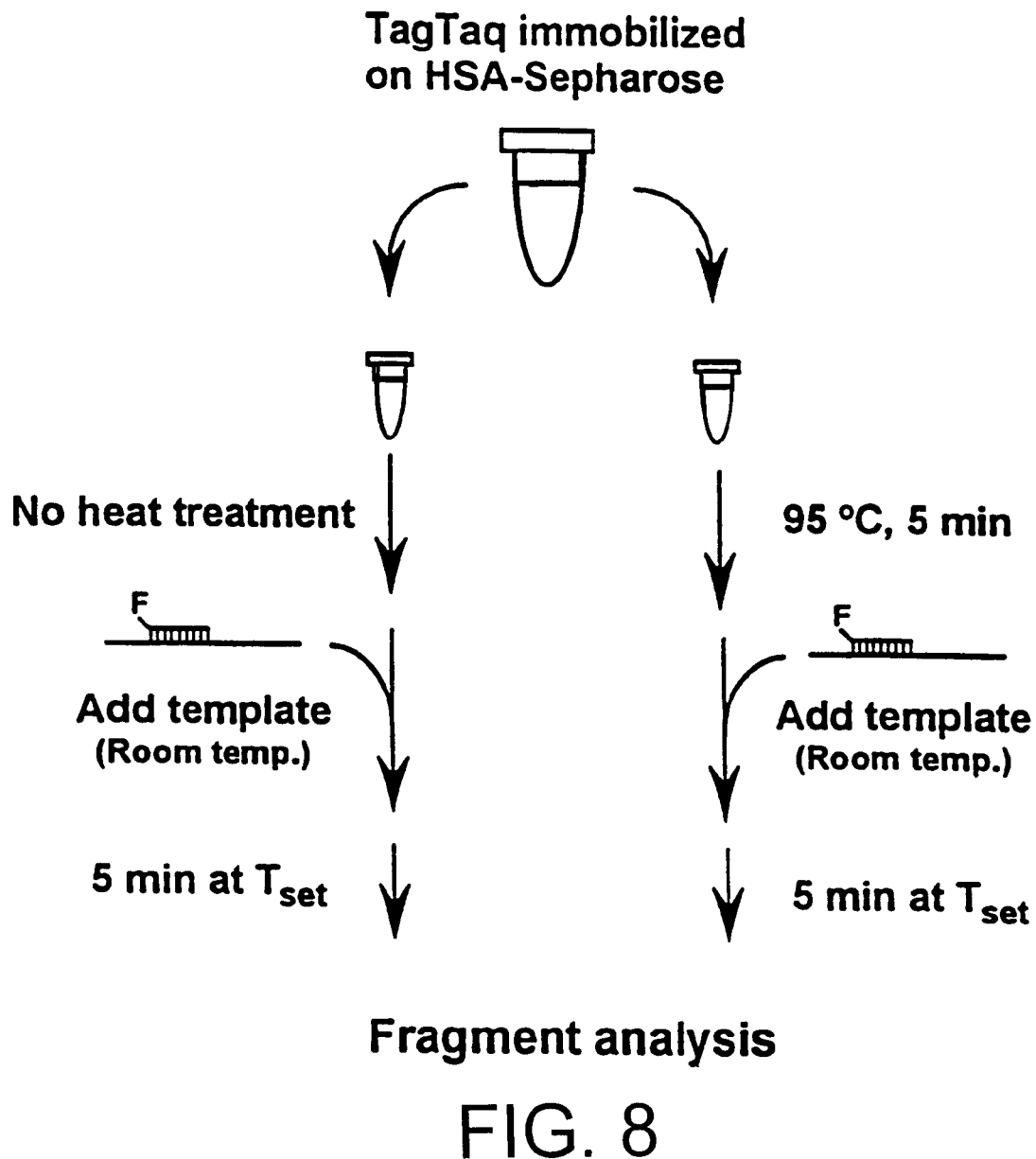
Figure 9:
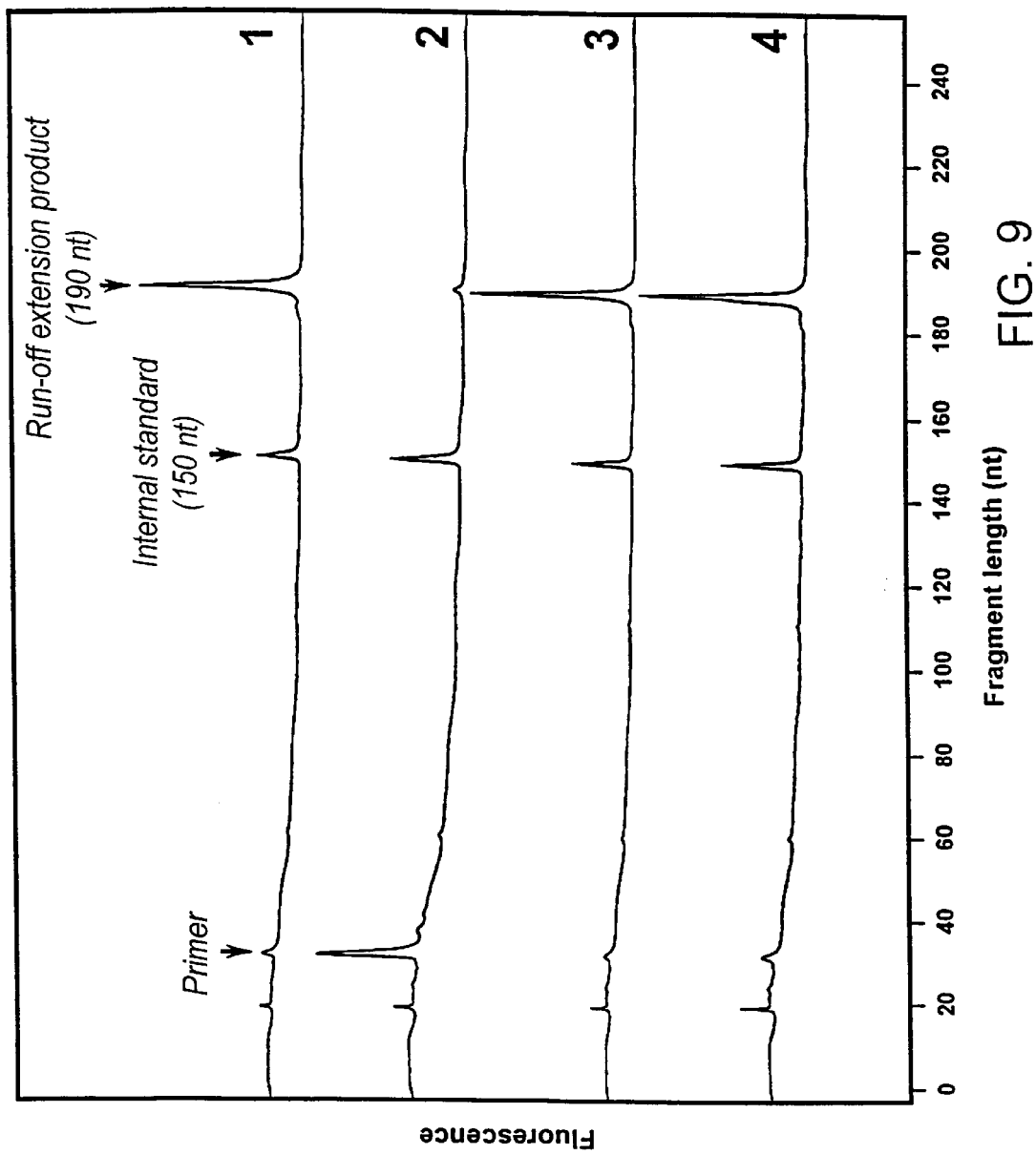

One μl from each sample was loaded on the gel;

FIG. 3 shows the results from the PCR amplification. Analysis of PCR products was performed by 1.5% agarose gel electrophoresis, stained with ethidium bromide. Lanes M show the molecular weight markers (bacteriophage λ DNA PstI digest); lanes 1–5, show PCR products using 0.3, 0.6, 1.2, 2.5 and 5.0 μl heat eluted Z-ΔTaq respectively; lanes 6–10, show PCR products using 0.3, 0.6, 1.2, 2.5 and 5.0 μl Z-ΔTaq—hIgG-Sepharose suspension (1 volume settled beads: 1 volume PCR buffer) respectively; lanes 11–15, show PCR products using 0.3, 0.6, 1.2, 2.5 and 5.0 μl BB-ΔTaq—HSA-Sepharose suspension (1 volume settled beads: 1 volume PCR buffer) respectively;

FIG. 4 shows a schematic drawing of the polymerase activity assay;

FIG. 5 shows the results from the polymerase activity assay. Fluorescence-based fragment analysis of extension products separated by 6% polyacrylamide gel electrophoresis. Lane 1, shows the FITC-labelled size markers 100, 150 and 200 bp; lane 2, shows the extension products from a 1 minute extension using 2 μl heat eluted Z-ΔTaq at 50° C. The reaction tube, containing all reagents except enzyme and the primer/single strand hybrid (starting material, see details in Example 1.4), was heated to 95° C. for 2 minutes and then chilled to 50° C. After 1 minute at 50° C. the enzyme was added to the tube, after an additional minute the primer/single strand hybrid was added and mixed using a pipette. Lane 3, shows the extension products from a 1 minute extension using 2 μl Z-ΔTaq—human IgG Sepharose suspension (1 volume settled beads: 1 volume PCR buffer) at 50° C. The reaction conditions were the same as described in lane 2. Lane 4, shows the extension products from a 1 minute extension using 2 μl of a 95° C.-treated Z-ΔTaq—human IgG-Sepharose suspension (1 volume settled beads: 1 volume PCR buffer) at 50° C. The reaction tube containing all reagents except the primer/single strand hybrid (starting material, see details in Example 1.4) was heated to 95° C. for 2 minutes and then chilled to 50° C. After 2 minutes at 50° C. the primer/single strand hybrid was added and mixed using a pipette. Lane 5, shows the FITC-labelled size markers 100, 150, 200 and 250 bp; lane 6, shows the extension products from a 2 minute extension using 1 μl BB-ΔTaq—hIgG-Sepharose suspension (1 volume settled beads: 1 volume PCR buffer) at 50° C. The reaction tube containing all reagents except enzyme was heated to 95° C. for 2 minutes and then chilled to 50° C. After 1 minute at 50° C. the suspension containing the immobilized enzyme was added and mixed using a pipette. Lane 7, shows the extension products from a 2 minute extension using 1 μl of a 95° C.-treated BB-ΔTaq—hIgG-Sepharose suspension (1 volume settled beads: 1 volume PCR buffer) at 50° C. The reaction tube containing all reagents except dNTP's was heated to 95° C. for 2 minutes and then chilled to 50° C. After 1 minute at 50° C. the dNTP's were added and mixed using a pipette. Lane 8, shows the sample described in lane 7 diluted 5 times in formamide solution (see below). Note that 5 μl from each sample was diluted 1:1 with deionized formamide containing Dextran Blue 2000; 10 mM EDTA; 10 mM NaOH; pH 8.2 and then denatured at 95° C. for 5 minutes and chilled on ice before loading. The arrows point at the expected extension product (190 bp);

FIG. 6 shows a schematic representation of the TagTaq fusion protein containing the multifunctional affinity fusion partner, Bio-His6-ABP, fused to the Taq DNA polymerase I (residues 3–832);

FIG. 7 shows the results from heat mediated elution. Analysis of material eluted from HSA-Sepharose at different temperatures was performed.by SDS-PAGE. Lane T, total proteins (starting material) on the HSA-Sepharose beads after affinity immobilization of the TagTaq fusion protein directly from an E. coli lysate. Lanes 65–95, material eluted after a 5 min incubation of the starting material at temperatures 65, 70, 75, 80, 85, 90 or 95° C., respectively. Lane M, marker proteins (sizes in kDa);

FIG. 8 shows the experimental outline with the two parallel alternative routes for analysis of the TagTaq polymerase activity;

FIG. 9 shows the results from the TagTaq polymerase activity assay. Lanes 1 and 2 correspond to heat released (right route) and immobilized (left route) samples, respectively, after extensions at 60° C. (Tset). Lanes 3 and 4 correspond to heat released (right route) and immobilized (left route) samples, respectively, and prior to the extension at 70° C. (Tset), the samples were incubated at 95° C. for 5 min.

Figure 11:
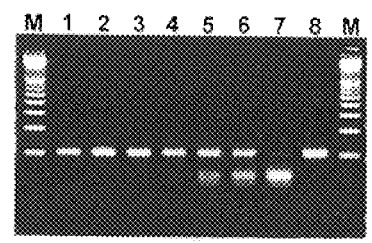
Figure 12:
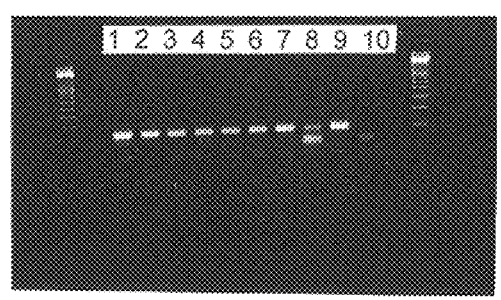
Figure 10:
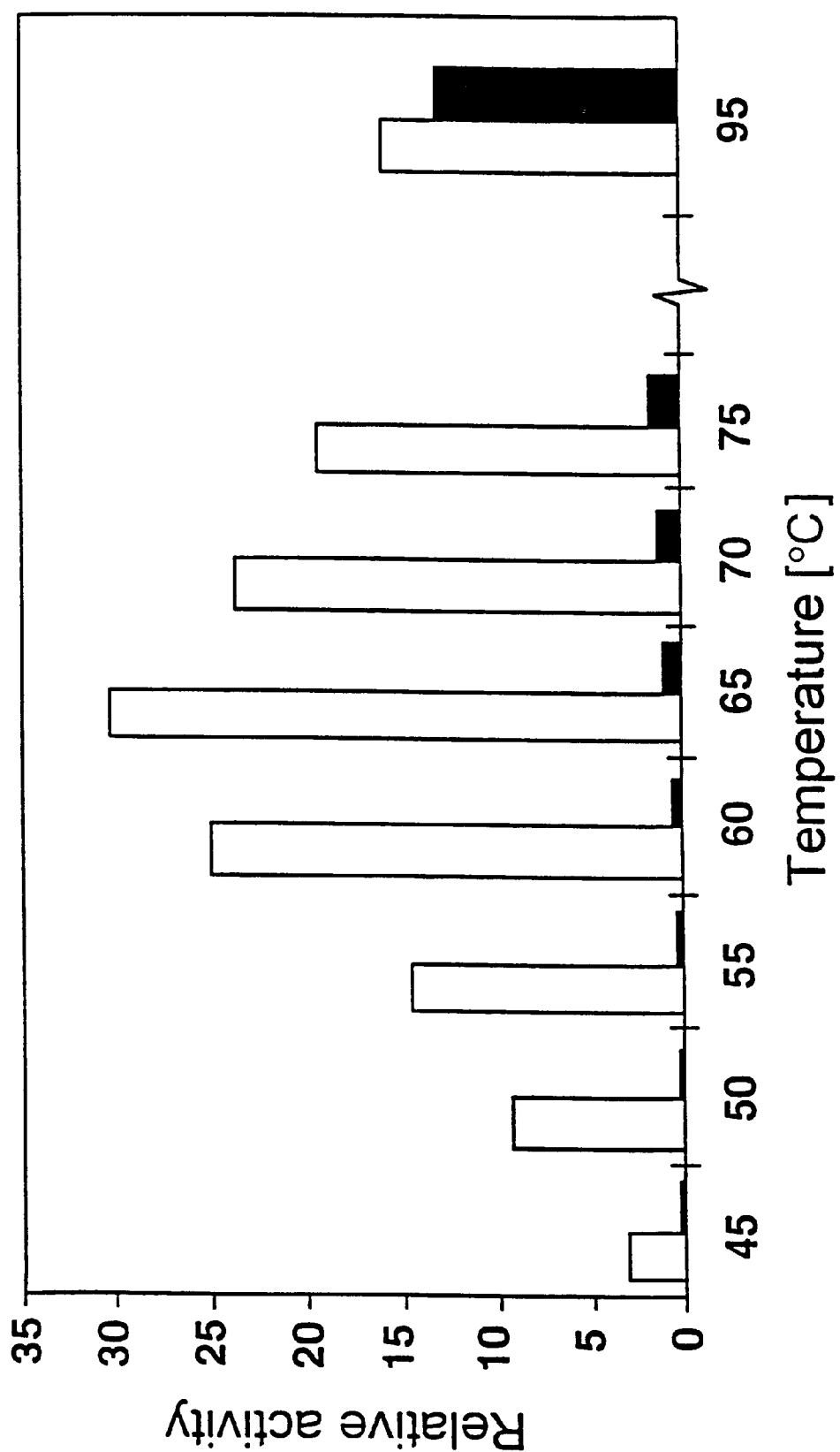

FIG. 10 shows a summary of the TagTaq fusion protein polymerase activities at different temperatures. The filled and open bars represent the relative activities of heat released (right route) and immobilized (left route), respectively, corresponding to the scheme shown in FIG. 8. The bars at 95° C. correspond to lanes 3 and 4 described in the legend to FIG. 9;

FIG. 11 shows the results of the PCR experiments using TagTaq and AmpliTaq polymerase analyzed by agarose gel electrophoresis. Lanes 1–3, K-ras gene amplification using 50 μg, 100 μg and 200 μg TagTaq fusion protein:HSA-Dynabeads, respectively; lanes 4–6, K-ras gene amplification using heat eluted TagTaq fusion protein from 50 μg, 100 μg and 200 μg TagTaq fusion protein: HSA-Dynabeads, respectively; lane 7, K-ras gene amplification using 2 units of AmpliTaq DNA polymerase, lane 8, as for lane 7 but after use of a conventional hot start procedure involving the addition of 2 units AmpliTaq DNA polymerase first at 94° C. The expected size of the K-ras amplicon was 104 bp. Lane M, DNA size marker (100 bp ladder);

FIG. 12 shows a 3% NuSieve GTG agarose gel with the PCR-products from kRAS-PCR using the different immobilised enzymes compared to free AmpliTaq and AmpliTaq added at 94° C. (conventional hot-start). Template: 25 ng of human genomic DNA per 30 μl reaction volume. Lane 1, 100 μg BBΔTaq-HSA-DB; lane 2, 100 μg ABP-Taq-HSA-DB; lane 3, 100 μg Aff2Taq-HSA-DB; lane 4, 100 μg Aff2Taq-streptavidin-DB; lane 5, 50 μg Aff2Taq-anti Biotin-RAM-DB; lane 6, 100 μg Aff2Taq-TaqStart antibody-RAM-DB; lane 7, AmpliTaq-TaqStart antibody-RAM-DB; lane 8, AmpliTaq (2u) positive control; lane 9, AmpliTaq (2u) added at 94° C. (conventional hot-start); and lane 10, AmpliTaq (2u) negative control.

DETAILED DESCRIPTION OF THE INVENTION

EXAMPLE 1

Figure 1:
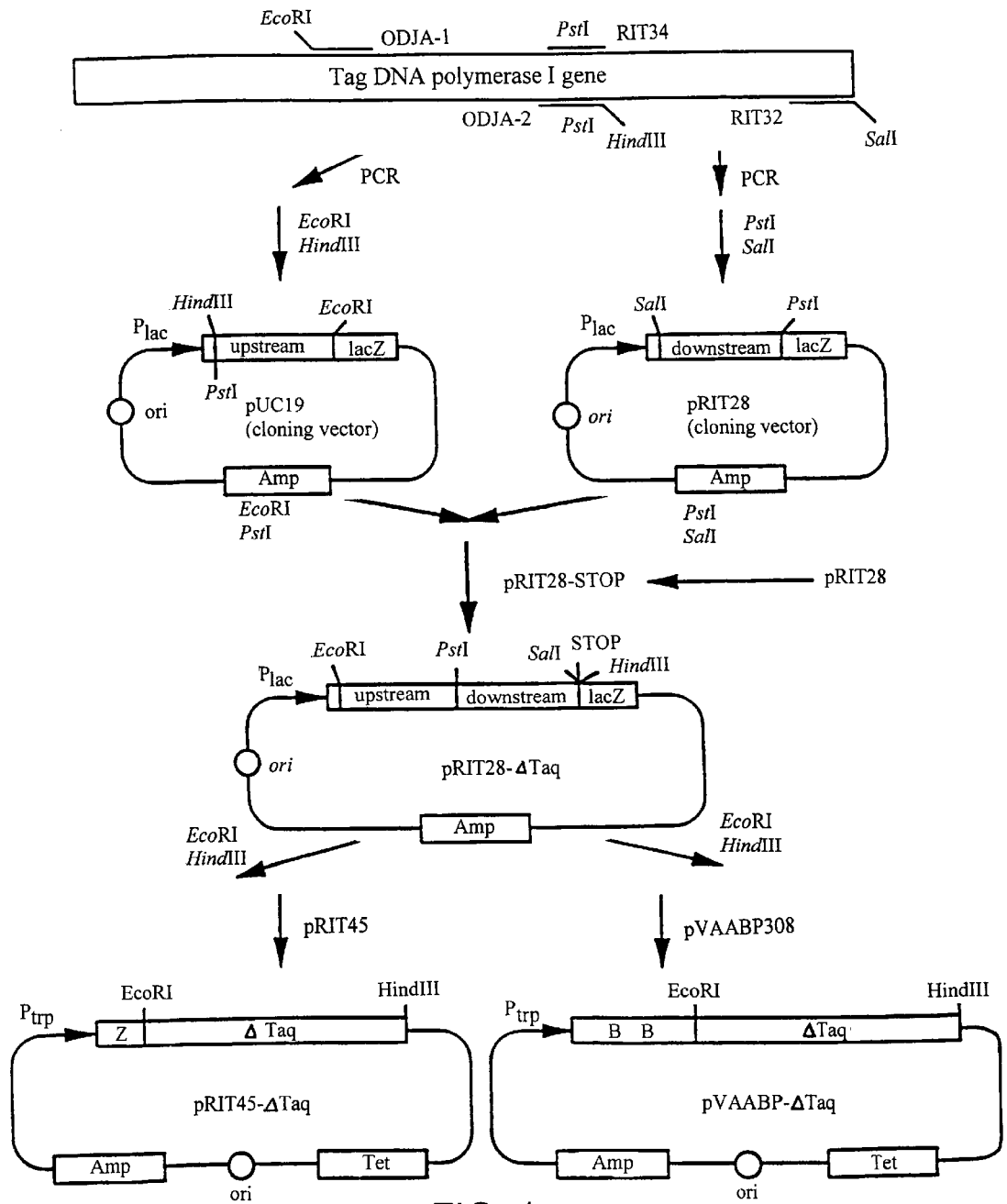
FIG. 1 shows a schematic cloning chart.

Cloning, Expression and Immobilization of N-Terminally Truncated TAQ DNA Polymerase I 1.1 Cloning and Construction of Expression Vectors All recombinant DNA manipulations followed standard procedures according to Maniatis et al. (Maniatis T., Fritsch E. F. and Sambrook J. (1982) Molecular Cloning: a laboratory handbook, Cold Spring Harbor Labratory, Cold Spring Harbor, N.Y.). The gene fragment, herein denoted ΔTaq, encoding a N-terminally truncated Thermus aquaticus (Taq) DNA polymerase I (residues 236–832) (Barnes W. M. (1992) Gene, 112, 29–35), was isolated by PCR in two parts, directly on the genomic DNA isolated from Thermus aquaticus, using primer pair ODJA-1: 5'-GGGAATTCCATGGACGATCTGAAGCTCTCCTG-3' SEQ ID NO: 2 and ODJA-2: 5'-CCCCAAGCTTCTGCAGGATCTTCTCCACGATG-3' SEQ ID NO: 2 for the upstream region and primer pair RIT34: 5'-GAAGATCCTGCAGTACCGGG-3' SEQ ID NO: 3 and RIT32: 5'-GGGTCGACCTCCTTGGCGGAGAGCCA-3' SEQ ID NO: 4 for the downstream region, see FIG. 1. The primers were designed, according to the sequence published by Lawyer et al. (Lawyer F.C ., Stoffel S., Saiki R. K., Myambo K., Drummond R. and Gelfand D. H. (1989) J. Biol. Chem., 262, 6427–6437), to enable assembly of the two regions using a unique PstI restriction site within the gene. The upstream region was amplified by PCR in a reaction tube containing (0.2 mM dNTP's; 10 mM KCl; 20 mM Tris-HCl, pH 8.2; 1.5 mM MgCl$_2$; 6 mM (NH$_4$)$_2$SO$_4$; 0.1% Triton X-100), 5 pmole of each primer (ODJA ½), approx. 20 ng genomic DNA and 3 units of Pfu DNA polymerase. The genomic DNA template was first denatured for 1.5 minutes at 97° C. The PCR-program (97° C., 1.0 minute: 63° C., 1.5 minutes; 72° C., 2.0 minutes) was repeated for 35 cycles in a Techne PHC-I thermocycler (Techne Inc. UK). The downstream region of DNA was amplified by PCR in a reaction tube containing 50 μl of PCR buffer (0.2 mM dNTP's; 50 mM KCl; 10 mM Tris-HCl, pH 8.3; 2.0 mM MgCl$_2$; 0.1% Tween 20), 5 pmoles of each primer (RIT 34/32), approx. 20 ng genomic DNA and 1.0 unit of Taq DNA polymerase. The genomic DNA template was first denatured for 5 minutes at 95° C. The PCR-program (96° C., 1.0 minute; 55° C., 1.5 minutes; 72° C., 2.0 minutes) was repeated for 35 cycles in a Techne PHC-I thermocycler (Techne Inc., UK). The upstream PCR-product was restricted with EcoRI and HindIII using the endonuclease sites introduced during the PCR and inserted into the multilinker of pUC19 (Yanisch-Perron C., Viera J. and Messing J. (1985) Gene, 33, 103–110), previously digested with the same enzymes. In all of the cloning procedures E. coli (RRIΔM15 (Rüther U. (1982) Nucl. Acids Res., 10, 5765–5772) were used as bacterial host. The downstream PCR-product was restricted with PstI and SalI using the internal PstI and the SalI site introduced during the PCR and inserted into the multilinker of pRIT 28 (Hultman T., Stahl S., Hornes E. and Uhlén M, (1989) Nucleic Acids Res., 17, 4937–4942), previously digested with the same enzymes. Correct nucleotide sequences were verified by solid-phase sequencing according to Hultman et al (Hultman T., Bergh S., Moks T. and Uhlén M. (1991) Biotechniques, 10, 84–93). After sequencing, the upstream Taq polymerase gene fragment was restricted with EcoRI and PstI and isolated from its cloning vector. The downstream gene fragment was restricted with PstI and SalI and isolated from its cloning vector. The two gene fragments were ligated together with pRIT28-STOP2, previously digested with EcoRI and SalI. The pRIT28-STOP2 was constructed from pRIT28 by insertion of a linker sequence 5'-GTCGACTAACTGCAG-3' SEQ ID NO: 5 (+strand) between the SalI and PstI sites of the cloning linker of pRIT28, resulting in an in-frame termination codon (TAA) directly after the SalI site. A schematic cloning chart is illustrated in FIG. 1.

Positive clones of the resulting pRIT28-ΔTaq were found by PCR-screening and restriction fragment mapping. After mapping, pRIT28-ΔTaq was digested with EcoRI and HindIII to release the ΔTaq encoding gene which was subsequent inserted into pRIT45 (Nilsson J., Nilsson P., Williams Y., Pettersson L., Uhlén M. and Nygren P.-Å. (1994) Eur. J. Biochem., 224, 103–108), previously digested with the same enzymes. The resulting vector, pRIT45-ΔTaq, encodes a tripartite fusion protein (herein denoted Z-ΔTaq) consisting of the first eight amino acids of the E. coli tryptophane (Trp) leader peptide, a synthetic monovalent IgG-binding domain Z (Nilsson B., Moks T., Jansson B., Abrahmsen L., Elmblad A., Holmgren E., Henrichson C., Jones A. and Uhlén M. (1987) Protein Eng., 1, 107–113), derived from staphylococcal protein A and an N-terminally truncated Taq DNA polymerase I. For this construct, the intracellular expression is under control of the E. coli trp promoter.

The ΔTaq gene was also inserted into pVAABP308 (Murby, M., Samuelsson, E., Nguyen, T. N., Mignard, L., Binz, H., Uhlén, M. and Stahl, S. (1995) Eur. J. Biochem. 230, 38–44) previously digested with EcoRI and HindIII. The resulting vector, pVAABP-ΔTaq, encodes a tripartite fusion protein (herein denoted BB-ΔTaq) consisting of the first eight amino acids of the Trp leader peptide, the serum-albumin binding region (BB) (Olsson A., Eliasson M., Guss B., Nilsson B., Hellman U., Lindberg M. and Uhlén M. (1987) Eur. J. Biochem., 168, 319–324) from streptococcal protein G and an N-terminally truncated Taq DNA polymerase I. For this construct, the intracellular expression is also under control of the E. coli trp promoter.

1.2 Gene Expression, Fusion Protein Purification and Immobilization

E. coli UT 5600 (Grodberg J. and Dunn J. J. (1988) J. Bacteriol., 170, 1245–1253) cells harbouring plasmids pRIT 45-ΔTaq and pVAABP-ΔTaq were grown overnight at 37° C. in shake flasks containing 20 ml Tryptic Soy Broth (Difco, USA) supplemented with 7 g/l of yeast extract (Difco, USA), tetracycline (Sigma, USA) (8 μg/ml) and ampicillin (Sigma, USA) (100 μg/ml). The overnight cultures were diluted 25-fold into shake flasks containing 1000 ml of the same media and grown at 37° C. Expression of the recombinant fusion proteins was induced at mid log phase ($A_{580}$=1) by the addition of β-indole acrylic acid (Sigma, USA) to a final concentration of 25 μg/ml. Cells were harvested four hours after induction, by centrifugation at approx. 5000 g for 5 minutes. The pelleted cells were resuspended in 30 ml washing buffer (50 mM Tris-HCl, pH 8.0; 0.15 M NaCl; 0.05% Tween 20) and lysed by sonication using a high intensity ultrasonic processor (Vibra cell™, Sonics & Materials, USA). Cell debris and denaturated proteins were pelleted by centrifugation at approx. 20000 g for 15 minutes. Purification of Z-ΔTaq and BB-ΔTaq from the supernatants was performed by affinity chromatography using human IgG-Sepharose (Pharmacia, Sweden) (Nilsson et al., 1994, supra) for Z-ΔTaq and human serum albumin (HSA)-Sepharose (Nygren, P.-Å., Eliasson M., Palmcrantz E., Abrahmsen L. and Uhlén M. (1988) J. Mol. Recognit., 1, 69–74) for BB-ΔTaq. The immobilized proteins were first washed with washing buffer and then with PCR buffer (50 mM KCl; 10 mM Tris-HCl, pH 8.3; 2.0 mM $MgCl_2$; 0.1% Tween 20). For analytical purity controls the fusion proteins were eluted with 0.2 M HAc pH 3.3 (Z-ΔTaq) and 0.5 M HAc pH 2.8 (BB-ΔTaq) and lyophilized. Preparative heat elution of Z-ΔTaq was performed by incubation of a sealed IgG-Sepharose column, equilibrated in PCR buffer, at 80° C. in a waterbath for 30 minutes. Hot (80° C.) PCR-buffer was then applied to the column and the flow through containing released Z-ΔTaq was collected. Columns with immobilized Z-ΔTaq and immobilized BB-ΔTaq were stored at 4° C. The eluted Z-ΔTaq was stored at -20° C. (50% glycerol was added).

Figure 2:
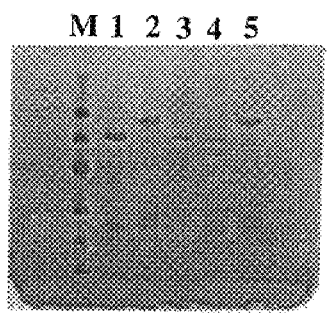
FIG. 2 shows results from the affinity purification of the Z-ΔTaq and BB-ΔTaq fusion proteins and the corresponding immobilized proteins. Analysis was performed by 10–15% SDS-PAGE, stained with Coomassie Brilliant Blue R-250 (Pharmacia, Sweden). M, Marker proteins with molecular masses in kDa (94, 67, 43, 30, 20.1 and 14.4). Lane 1, human IgG-affinity purified (HAc eluted) Z-ΔTaq fusion protein; lane 2, HSA-affinity purified (HAc eluted) BB-ΔTaq fusion protein; lane 3, hIgG-affinity purified (heat eluted) Z-ΔTaq fusion protein (2.0 μl was diluted 5 times in loading buffer); lane 4, immobilized Z-ΔTaq fusion protein (2.0 μl (1 volume settled beads: 1 volume .PCR buffer) was diluted 5 times in loading buffer (non-reducing conditions); lane 5, immobilized BB-ΔTaq fusion protein (2.0 μl (1 volume settled beads: 1 volume PCR buffer) was diluted 5 times in loading buffer (non-reducing conditions)).

The purity of the proteins was analyzed by SDS/PAGE using the PHAST™ system (Pharmacia, Sweden), FIG. 2. The analysis of the IgG-affinity purified Z-ΔTaq fusion protein showed that the fusion (76.5 kDa) (lane 1) was stable and produced at approximately 3 mg/l culture (data not shown). In parallel the analysis showed that the BB-ΔTaq fusion protein was almost exclusively of full-length (94.5 kDa) (lane 2) and produced at approximately 5 mg/l culture (data not shown). Equal amounts of the free (lane 3) and immobilized (lanes 4–5) ΔTaq polymerase were determined by comparing the band intensities. It can be seen that small amounts of IgG-fragments (~25 kDa and ~50 kDa) are detached from the affinity column when elution is performed by low pH (lane 1) but not when elution is carried out by heat (lane 3). IgG fragments are also evident when the Z-Taq fusion protein immobilized to human IgG-Sepharose is boiled in SDS/PAGE loading buffer (lane 4). In a similar manner, weak detachment of HSA (67 kDa) can be observed when BB-ΔTaq fusion protein immobilized to HSA-Sepharose is boiled in SDS/PAGE lading buffer (lane 5).

1.3 Polymerase Chain Reaction Amplification using Free Z-ΔTaq, Immobilized Z-ΔTaq and Immobilized BB-ΔTaq The amplification test was performed on a Gene ATAQ Controller (Pharmacia, Sweden). The reactions were performed in 50 μl of PCR buffer (0.2 mM dNTP's; 50 mM KCl; 10 mM Tris-HCl, pH 8.3; 2.0 mM $MgCl_2$; 0.1% Tween 20), 5 pmoles of each primer RIT27 and RIT30 (Hultman et al., 1991, supra) respectively and approx. 10 pg pRIT28 target DNA, resulting in a 248 bp fragment. The PCR program (96° C., 30 s; 69° C., 2 minutes) was repeated for 35 cycles. Different amounts of free and immobilized enzyme were tested, see FIG. 3.

The results show that both free and immobilized enzymes (which are released during the first cycle), are functional in the polymerase chain reaction. The different amounts of enzymes tested, indicates similar activities in the three different forms of ΔTaq used in the PCR test, shown by the parallel decrease in fragment intensity for decreased amount of enzyme. Note, that immobilized BB-ΔTaq fusion protein has an apparent 2-fold higher activity per volume settled beads compared to immobilized Z-ΔTaq.

1.4 Polymerase Activity Assay Using Immobilized and Free Enzyme

The DNA-polymerase activity of free Z-ΔTaq, immobilized Z-ΔTaq and immobilized BB-ΔTaq was tested in an extension reaction at 50° C. using a FITC-labelled extended universal sequencing primer, FITC-USPEXT (5'-Fluorescein-CAGTCACGACGTTGTAAAACGGCCAGT-3' SEQ ID NO: 6) annealed to a linear single stranded DNA. The general protocol is illustrated schematically in FIG. 4. The single stranded DNA was prepared by immobilization of the 248 bp PCR-product (appr. 600 ng), see above, to 200 μg streptavidin-coated paramagnetic beads (M-280, Dynal AS, Norway), previously washed with washing buffer (TE buffer (10 mM Tris, pH 7.5; 1 mM EDTA) supplemented with 2 M NaCl, 1 mM 2-mercaptoethanol and 0.1% Tween 20) via the biotinylated complementary strand (Hultman et al., 1991; supra). A neodymium-iron-boron permanent magnet (Dynal, Norway) was used to sediment beads in the tubes during supernatant removal and washing procedures. The PCR mixture (40 μl) was first diluted 1:1 in washing buffer, mixed with the beads and incubated for 30 minutes at room temperature (sedimented beads were resuspended twice using a pipette). The beads were washed first with washing buffer and then with TE buffer. The non-biotinylated strand was eluted by incubation of beads in 10 μl 0.1 M NaOH for 5 minutes at room temperature. The supernatant containing the eluted strand was removed, placed in a new tube and neutralized with 6 μl 1/6 M HCl.

Starting material for the subsequent extension experiments was prepared prior to mixing with the other reaction materials by annealing of the FITC-USPEXT primer to the single stranded DNA, by first heating to 95° C. for 30 s and then chilling to room temperature for the experiments showed in lanes 2–4, FIG. 5. However, in the experiments showed in lanes 6–7 the annealing was performed simultaneously along with the extension experiment. In all experiments the heating and chilling were performed by 1° C./2s. The extension reactions were performed in 25 μl PCR-buffer (20 mM Tris-HCl, pH 8.3; 50 mM KCl; 2.0 mM $MgCl_2$; 0.1% Tween 20) supplemented with 1 pmole FITC-USPEXT and 4.0 μl (Z-ΔTaq experiments) or 8.0 μl (BB-ΔTaq experiments) of the eluted and neutralized 248 bp single stranded DNA and 0.5 mM dNTP's. Two microliters heat eluted Z-ΔTaq, 2.0 μl Z-ΔTaq—human IgG-Sepharose suspension (1 volume settled beads: 1 volume PCR buffer) or 1.0 μl BB-ΔTaq—HSA-Sepharose suspension (1 volume settled beads: 1 volume PCR buffer) were used respectively. The reaction tubes were incubated on a Gene ATAQ Controller (Pharmacia), see figure legend for the different experiment conditions. The extension reactions were stopped by addition of 25 µl stop solution (deionized formamide containing Dextran Blue 2000; 5% SDS; 10 mM EDTA; 10 mM NaOH), immediately put on ice and stored at −20° C. The extension products were analyzed on an ALFT™ DNA Sequencer gel (6% polyacrylamide), using the Fragment Manager software (Pharmacia) together with an external standard (Sizer 50–500, Pharmacia) for quantification and size determination, see Table 1 and FIG. 5.

The analyses of the experiments clearly show the differences between immobilized and free enzyme in the ability to extend the primer/single strand hybrid at 50° C. The fact that a high percentage of the two different DNA polymerases are immobilized during the extension time at 50° C. is seen by comparing the area of the expected peak (190 bp fragment) between the different experiments. The area of the 190-peak arising from free enzyme and enzyme released from the beads by the heat cycle 95° C. to 50° C. is more than 15 times (Z-Taq) and 20 times (BB-ΔTaq) increased respectively (estimated by the Fragment Manager) than the area of the 190-peak arising from enzyme released from the beads which had only been heated up to 50° C. This means that immobilization of Z-ΔTaq and BB-ΔTaq using human IgG-Sepharose and HSA-Sepharose respectively prevents and inhibits extension of the primer/single strand hybrid up to 50° C. The release of the two DNA polymerase fusion proteins from the affinity ligand by heating to 95° C. indicates the use of these two fusion patients in "HOT START" PCR.

TABLE 1

Polymerase activity of free, immobilized and heat-released Taq polymerase as assessed by quantitation of the 190-bp peaks shown in FIG. 5.

| Polymerase | Peak area |
| --- | --- |
| Free ZΔTaq | 9912* |
| Immobilized ZΔTaq | 594 |
| Heat-released ZΔTaq | 8375* |
| Immobilized BBΔTaq | 1790 |
| Heat-released BBΔTaq | 35930 |

*Calculated partial peak area as shown in lane 2 and lane 4 of FIG. 5.

EXAMPLE 2

Cloning, Expression and Immobilization of Full Length TAQ DNA Polymerase I

Bacterial Strains and Plasmid Vectors

E. coli strains RRIΔM15 (Ruther, 1982, supra) and BL21 (DE3)pLysS (Novagen, Inc., Madison, WI, USA) were used as bacterial hosts for cloning and gene expression, respectively. Thermus aquaticus strain YT-1 (ATCC 25104, The American Type Culture Collection, Rockville, MD, USA) was used as source for the gene encoding Taq DNA polymerase I. Plasmid pGEM®-T (Promega Corporation, Madison, Wis., USA) and pAff2c were used as vectors. The latter vector is adapted for fusion of target proteins to a tripartite affinity tag, Bio-His6-ABP, consisting of a recognition sequence for in vivo biotinylation (Schatz, P. J. (1993) Bio/Technology 11: 1138–1143), a His6 peptide (Hochuli, E., Bannwarth, W., Dobeli, H., Gentz, R. and Stuber, D. (1988) Bio/Technology 6: 1321–1325) and parts (residues 146–266) of the serum albumin binding region (ABP) from streptococcal protein G (Nygren et al., 1988, supra) (FIG. 6). ABP, in common with BB used in Example 1, binds to HSA. However ABP is smaller than BB and consists of two minimal HSA binding domains. The domains of Bio-His6-ABP can be used separately or in combination for purification, immobilization and detection of fusion proteins. For example, this single fusion partner allows for the evaluation of three separate purification and immobilization strategies for a fused target protein (i) biotin-avidin (streptavidin) (ii) hexahistidyls-immobilized metal ions and (iii) albumin binding protein (ABP)-HSA. In the present example, the ABP tag has been used as preliminary data indicates that its interaction with human serum albumin ($K_{aff} \sim 10^9$ $M^{-1}$) is disrupted at elevated temperatures. In addition, any leakage of the ligand (HSA) would be unlikely to affect the PCR, since its homolog BSA is frequently included in PCR buffers at relatively high concentrations to improve PCR performance.

Vector pAff2c was constructed as follows. A gene fragment encoding a divalent synthetic IgG binding affinity handle, ZZ (Nilsson et al., 1987, supra), derived from staphlococcal protein A (SpA), was amplified from plasmid pEZZT308 (Nygren et al., 1988, supra) using a standard PCR protocol (Hultman et al., 1989, supra). The oligonucleotide LAMA7, 5'-CCCTGAT-CACCATGGGCGCAACACGATGAAGCCGTAG-3' SEQ ID NO: 7, was used as an upstream primer, and the oligonucleotide LAMA10, 5'-GGGGGATCCATGTAGTGAGCGAAGGTACCATT CGCGTCTACTTTCGGCGCC-3' SEQ ID NO: 8, was used as the downstream primer, to generate fragments corresponding to frame c. Upstream restriction sites for BclI and NcoI were introduced by LAMA7, and sites for KpnI and BamHI by the downstream primer. In addition, sequences for cleavage of produced fusion proteins by His64Ala-subtilisin (Carter, P., Nilsson, B., Burnier, J. P., Burdick, D. and Wells, J. A. (1989) Proteins Struct. Funct. Anal. 6, 240–248) were introduced downstream of the ZZ fragment by the downstream primer. The ZZ-encoding PCR fragments were cleaved with BclI and BamHI and introduced into the BamHI site of plasmid pET21a(+) (Novagen Inc., Madison, Wis.), resulting in the expression vector pT7-TZZc. Correct insertion was verified by solid-phase DNA sequencing (Hultman, et al., 1989, supra).

The pT7-ABPc expression vector was constructed from the pT7-TZZc vector. A DNA fragment encoding ABP was obtained by PCR amplification from plasmid pVABP308 (Murby et al., 1995, supra) using LAMA17, 5'-CCGAATTCG-CTAGCTTAGCTGAAGCTAAAGTCTTAG-3SEQ ID NO: 9, as an upstream primer and LAMA18, 5'-CCGGTACCAGGTAATGCAGCTAAAATTTCATC-3' SEQ ID NO: 10, as a downstream primer, respectively. An upstream restriction site for NheI and a downstream site for KpnI were introduced by LAMA17 and LAMA18, respectively. The PCR fragment was cleaved with restriction enzymes NheI and KpnI and introduced into the pT7-TZZc vector previously digested with the same restriction enzymes. Correct insertion was verified by solid-phase DNA sequencing (Hultman et al., 1989, supra). The resulting vector was denoted pT7-ABPc.

Plasmid pT7ABPIIc was created by inserting a phosphorylated linker composed of Grto-1: 5'-AATTTGGAAGCTCTGTTCCAGGGTCCG-3' (SEQ ID NO:11) (sense strand) and Grto-2: 5'-AATTCGGACCCTGGAACAGAGCTTCCA-3' (SEQ ID NO:12) into the unique EcoRI site of pT7-ABPc. The linker translates into EALFQGP (SEQ ID NO:23), a recognition sequence for the 3C protease as deduced from the sequence of coxsackievirus B3 polyprotein.

Plasmid pAAf2c was constructed using pT7ABPIIc as follows: Two DNA fragments encoding an in vivo biotinylated peptide (Schatz, 1993, supra) and a His6 peptide with two glycine residues at the C-terminal side, respectively, were created by synthesizing four oligonucleotides with flanking aNheI (5') and NheI (3') protrusions, Biotin-5' (coding), 5'-CT AGT AGC CTG CGC CAG ATC CTG GAC AGC CAG AAA AT(C/G) GAA TGG CGC AGC AAC GCT GGT GGT G-3' SEQ ID NO: 13, Biotin-3, 5'-CT AGC ACC ACC AGC GTT GCT GCG CCA TTC (C/G)AT TTT CTG GCT GTC CAG GAT CTG GCG CAG GCT A-3' SEQ ID NO: 14, His-5' (coding), 5'-CT AGT CAC CAC CAC CAC CAC CAC GGT GGT G-3' SEQ ID NO: 15 and His-3', 5'-CT AGC ACC ACC GTG GTG GTG GTG GTG GTG A-3' SEQ ID NO: 16. The His-5' and His-3' oligonucleotides were 5'-phosphorylated, mixed, heated to 95° C. and cooled to room temperature. Non-phosphorylated Biotin-5' and Biotin-3' oligonucleotides were also mixed, heated to 95° C. and cooled to room temperature. The two DNA fragments were inserted in a stepwise manner into a unique NheI site in pT7-ABPIIc beginning with the Biotin-5'/3' fragment. After each step, correct insertion was verified by restriction fragment mapping and solid phase DNA sequencing (Hultman et al., 1989, supra). The resulting vector was denoted pAff2c.

2.1 Cloning and Construction of Expression Vectors

All recombinant DNA manipulations followed standard procedures according to Maniatis et al. (Maniatis T., Fritsch E. F. and Sambrook J. (1982) Molecular Cloning: a laboratory handbook, Cold Spring Harbor Labratory, Cold Spring Harbor, N.Y.).

Genomic DNA was isolated from Thermus aquaticus essentially as described previously (Lawyer et al., 1989, supra). The gene encoding Taq DNA polymerase I was amplified from genomic DNA by PCR, essentially according to Engelke and coworkers (Engelke, D. R., Krikos, A., Bruck, M. E. and Ginsburg, D. (1990) Anal. Biochem. 191: 396–400), but with an alternative 3'-PCR primer (carboxyl terminal): 5'-CAC CAC GCG TCG ACC TCC TTG GCG GAG AGC CAG TCC TC-3' SEQ ID NO: 17 and with formamide (5% final conc.) in the PCR mixture. The PCR fragment was ligated into pGEM®-T according to the manufacturer's instructions. Positive clones were selected by plasmid restriction mapping. Using the restriction sites introduced by the PCR primers, EcoRI (upstream) and SalI (downstream), the Taq DNA polymerase I gene was isolated and introduced into EcoRI and SalI digested pAff2c by ligation. In order to create an in-frame termination codon (TAA) a linker (5'-TCG ACT AAC TGC AGG CAT GCA-3' SEQ ID NO: 18) (sense); 5'-AGC TTG CAT GCC TGC AGT TAG-3' SEQ ID NO: 19 (antisense) was inserted between the SalI and HindIII sites of pAff2c. Thus, the resulting plasmid pAff2-Taq encodes the Bio-His6-ABP tag followed by the Taq DNA polymerase I (residues 3–832)(Ollis, D. L., Brick, P., Hamlin, R., Xuong, N. G. and Steitz, T. A. (1985) Nature 313: 762–766), designated TagTaq (FIG. 6).

2.2 Gene Expression, Fusion Protein Purification and Immobilization

E. coli cells harbouring the plasmid pAff2-Taq were grown overnight at 37° C. in a shake-flask containing 50 ml tryptic soy broth (30 g/l, Difco, Detroit, Mich., USA) supplemented with 5 g/l yeast extract (Difco), 100 μg/ml ampicillin and 34 μg/ml chloroamphenicol. On the following morning, the culture was diluted 25-fold into shake-flasks containing the same media as above but without chloroamphenicol and grown at 30°C. Isopropyl β-D-thiogalactosidase (IPTG) and d-biotin was added to final concentrations of 1 mM and 0.1 mM respectively, when the optical density (A580 nm) of the culture was approximately 1. Cells were grown for 5 hours, harvested by centrifugation, resuspended in 30 ml washing buffer (50 mM Tris-HCl, pH 8.0, 0.2 M NaCl, 0.05% Tween 20®, 1 mM EDTA) and stored at −20° C. Thawed cells were sonicated, centrifuged at 30000 g for 20 min followed by filtration (0.45 μm filter) of the supernatant. The solution was immediately applied onto a 5 ml human serum albumin (HSA)-Sepharose column at room temperature as previously described (Nygren et al., 1988, supra). After loading, the column was washed with 200 ml washing buffer followed by 60 ml PCR buffer (10 mM Tris-HCl, pH 8.5, 50 mM KCl, 2 mM $MgCl_2$, 0.1% Tween 20®). The TagTaq fusion protein as immobilized to HSA-Sepharose was stored at 4° C. in PCR buffer or eluted with 0.5 M HAc, pH 2.8 after a pre-wash with 60 ml 10 mM $NH_4Ac$, pH 5.5. Relevant eluted fractions were pooled and loaded on PD-10 columns (Pharmacia Biotech, Uppsala, Sweden) for buffer exchange to 2x storage buffer (40 mM Tris-HCl, pH 8.0, 200 mM KCl, 0.2 mM EDTA, 2 mM DTT, 1.0% Tween 20®, 1.0% Nonidet P40®) and stored at 4° C. The amount of affinity purified fusion protein was estimated from absorbance measurement of the HAc eluate by using an extinction coefficient of 1.0 $cm^2/mg$.

The resulting 110 kDa fusion protein designated TagTaq was produced in E. coli and purified by HSA-affinity chromatography from a homogenized cell lysate. Analysis by SDS-PAGE showed that the majority (appr. 90%) of the material recovered after elution with pH 2.8 was of full-length (data not shown). Using this one-step purification procedure, the expression level of TagTaq fusion protein was calculated to approximately 3 mg/l culture.

2.3 Heat Elution of Immobilized Fusion Protein

Equal volumes of settled HSA-Sepharose beads with immobilized TagTaq fusion protein and PCR buffer were mixed, whereafter 50 μl aliquots (approx. 25 mg immobilized TagTaq fusion protein) were transferred to individual tubes. The tubes were heat incubated in a PCR 2400 thermocycler (Perkin Elmer, Norwalk, Conn., USA) for 5 min at different temperatures (45, 50, 55, 60, 65, 70, 75, 80, 85, 90, or 95° C.). Immediately after heat treatment, the beads were resuspended, sedimented by centrifugation and the supernatant transferred to a new tube. As a control, one tube was not heat treated. SDS-PAGE analyses were performed using 8–25% gradient gels and the PhastSystem™ (Pharmacia Biotech, Uppsala, Sweden) followed by staining with Coomassie Brilliant Blue R-350 (Pharmacia Biotech, Uppsala, Sweden). The samples were prepared by mixing 8 μl heat eluted material with 2 μl 5x loading buffer (100 mM Tris-HCl , pH 8.0, 5 mM EDTA, 12.5 mg/ml SDS, 25% 2-mercaptoethanol, 0.5 mg/ml bromophenol blue). The reference sample was prepared by taking 8 μl of suspended beads and mixing them with 2 μl 5x loading buffer.

An analysis by SDS-PAGE of collected supernatant samples showed that no significant release of the fusion protein was observed at temperatures below 700° C. (FIG. 7). However, at temperatures above 70° C., increasing amounts of TagTaq fusion protein (110 kDa) were observed in the supernatants, with the largest amounts in the sample corresponding to incubation at 95° C. Taken together, the data suggests that the HSA-ABP interaction is broken in the same temperature range routinely desired for initiation of polymerase activity in hot start PCR protocols. It is noteworthy that no or little of the HSA ligand (67 kDa) is present in the supernatants even at 95° C., indicating that the covalent coupling to the gel matrix is unperturbed even under these conditions.

2.4 DNA Polymerase Activity Assay Using Immobilized and Free Enzyme

The polymerase activity was investigated (essentially as described in Example 1.4) for TagTaq fusion protein immobilized to HSA-Sepharose beads (FIG. 8) by extension at different temperatures of a fluorescein labeled primer: FITC-USPEXT (5'-fluorescein-CAG TCA CGA CGT TGT AAA ACG GCC AGT-3' SEQ ID NO: 20), annealed to a linear (248 nt) single stranded DNA prepared in the following manner (essentially as described in Example 1.3). Multiple PCRs were carried out in total volumes of 50 µl PCR buffer containing 0.2 mM dNTP's, 5 pmoles of each primer RIT27 and RIT30 (biotinylated)(Hultman et al., 1989, supra), approximately 10 pg pRIT28 (Hultman et al., 1991, supra) plasmid target DNA and 1 U AmpliTaq (Perkin Elmer, Norwalk, Conn., USA). The PCR program used was 95° C. for 5 min followed by 35 cycles of (95° C., 30 s, 70° C., 2 min) and a final extension at 70° C. for 7 min. Immobilization of the pooled biotinylated PCR-products (400 µl) was performed by mixing with 2 mg streptavidin-coated paramagnetic beads (Dynabeads M-280 Streptavidin, Dynal A. S, Oslo, Norway) suspended in 400 µl washing buffer (TE buffer (10 mM Tris-HCl, pH 7.5, 1 mM EDTA), supplemented with 2 M NaCl, 1 mM 2-mercaptoethanol and 0.1% Tween 20®) with a subsequent incubation at room temperature. Sedimented beads were resuspended twice during the incubation. A neodynium-iron-boron permanent magnet (MPC, Dynal A. S, Dynal A. S, Oslo, Norway) was used to sediment the beads. After PCR-product immobilization the beads were washed with washing buffer and TE buffer. The non-biotinylated strand was eluted by treating the beads with 100 µl 0.1 M NaOH for 5 min at room temperature. The supernatant containing the eluted strands was transferred to a separate tube and neutralized with 60 µl 0.1667 M HCl. The extension templates were prepared in batch by mixing 17 µl FITC-USPEXT primer (1 pmol/µl) with 153 µl of the single stranded complementary DNA and heating to 95° C. for 30 s followed by cooling to room temperature.

For the following extension experiments, separate tubes were arranged containing 5 µl 10x PCR buffer, 5 µl 20 mM dNTP's, 28.5 1 H20 and 1.5 µl suspended TagTaq: HSA-Sepharose (approx. 40 ng fusion protein). The TagTaq: HSA-Sepharose stock solution was prepared by mixing 50 µl settled HSA-Sepharose with immobilized TagTaq fusion protein and 1 ml PCR buffer. The samples were processed by two alternative routes (FIG. 8) of which one involved a pre-incubation step at 95° C. for 5 min. Ten microliter of extension template solution were added at room tempeature to both heat-treated and non heat-treated samples, which were in a pairwise manner incubated at different temperatures. After 5 min the reactions were stopped by addition of 50 µl loading dye (100% deionized formamide, 5 mg/ml Dextran Blue 2000, Pharmacia Biotech, Uppsala, Sweden) supplemented with 20 mg/ml SDS and 10 mM EDTA, and cooled to 4° C. in the PCR-block. The tubes were stored at −20° C. The investigated temperatures were (45, 50, 55, 60, 65, 70 and 75° C.). In a control experiment the extension was performed at 70° C. after an initial incubation at 95° C. for 5 min. The PCR 2400 instrument was used for all heat incubations and PCR reactions.

Evaluation of Activity Assay

The extension products from the activity assay were analyzed on a 6% polyacrylamide gel mounted in an ALF DNA Sequencer™ (Pharmacia Biotech, Uppsala, Sweden). An external marker (Sizer 50–500, Pharmacia Biotech, Uppsala, Sweden) was used for subsequent fragment length estimations and an internal standard (150 nucleotides, Sizer 150, Pharmacia Biotech, Uppsala, Sweden) for product quantification. Prior to loading the samples were prepared by mixing 1 µl sample, 2 µl internal standard and 7 al loading dye or 4.5 µl sample, 2 µl internal standard and 9 µl loading dye, followed by heating to 95° C. for 5 min, and cooling on ice. Samples analyzed in FIG. 9 were prepared identically. Full extension of the template strand results in the production of fluorescence labeled 190 nt run-off fragments, suitable for detection and quantification using a DNA sequencer electrophoresis system. Fragment Manager 1.1 Software (Pharmacia Biotech, Uppsala, Sweden) was used for fragment size calculations and peak quantification. The peak area ratios shown in FIG. 10 were calculated by the formula: (product peak area x dilution factor)/internal standard peak area.

The results from the incubation of free TagTaq protein at 60° C. shows a major peak corresponding to a fragment size of 190 nt, resulting from successful extension of almost all available substrate templates as indicated by the small peak at 30 nt corresponding to remaining non-extended primers (FIG. 9, lane 1). In contrast, TagTaq protein: HSA-Sepharose incubated with the substrate at the same temperature resulted in only very small amounts of the 190 nt extension product. Instead, a major peak was observed at 30 nt suggesting that almost all substrate templates remained unextended under these conditions (FIG. 9, lane 2). It is noteworthy that no extension products of intermediate lengths can be observed suggesting that extensions are either complete or not initiated. This is also supported by the approximately equal peak areas for unextended and extended samples.

The results from incubations of parallel samples also at other temperatures in the range of 45° C. to 75° C. are summarized in FIG. 10, which shows the relative activities as calculated from ratios between peak areas corresponding to the 190 nt extension product and the internal standard 150 nt fragment. Free TagTaq protein shows a high relative activity at all temperatures tested with an apparent maximum at 65° C. Samples containing TagTaq immobilized to HSA-Sepharose show generally very low relative activities with a small increase at 65° C.–75 C. To further rule out the possibilities that the immobilized preparation of TagTaq was inactive or that HSA-Sepharose acted as an inhibitor for the polymerase activity, both free (i.e. pre-heat released) and TagTaq: HSA-Sepharose samples containing the substrate template were subjected to an authentic first PCR cycle with subsequent incubations at 95° C. and 70° C. Taken together, the results shown in FIG. 9 (lanes 3 and 4) and FIG. 10 (95° C. samples) indicate that TagTaq indeed is active in the presence of HSA-Sepharose, but only after incubation at a temperature high enough to break the ABP-HSA affinity interaction.

The slight decrease in relative activity observed for free Taq DNA polymerase fusion protein at temperatures above 65° C. can probably be explained by partial strand separation of the heteroduplex DNA used as extension substrate. Using a more stable substrate with a higher $T_{melting}$ temperature one would expect a maximum polymerase activity at approximately 75° C., according to previous studies on the optimal temperature for the recombinant Taq DNA polymerase (Lawyer, F. C., Stoffel, S., Saiki, R. K., Chang, S.-Y., Landre, P. A., Abramson, R. D. and Gelfand, D. H. (1993) PCR Methods Appl. 2: 275–287).

The ABP affinity fusion partner is still functional after 30 PCR cycles, allowing post-PCR re-immobilization of Taq DNA polymerase fusion protein onto fresh HSA-Sepharose. This would facilitate the removal of the DNA polymerase from a reaction mixture after PCR and thereby allow efficient endonuclease restriction without prior purification of the PCR product, usually performed to circumvent polymerase dependent fill-in reactions of generated protrusions.

2.5 Hot Start PCR

The TagTaq fusion protein was immobilized onto HSA-coated super-paramagnetic Dynabeads M-280 (Dynal A. S, Oslo, Norway) by resuspending 10 mg of HSA-coated Dynabeads in 0.5 ml storage buffer and adding 0.5 ml TagTaq fusion protein solution (approx. 100 µg/ml). The suspension was incubated at room temperature for 60 minutes, with gentle agitation. The beads were washed with 4×1 ml storage buffer. After washing, the beads were resuspended to a concentration of 10 mg beads/ml storage buffer and stored at 4° C. Hot start PCR was demonstrated by amplifying a 104 bp amplicon of the human K-ras oncogene using the primers denoted Forward (5'-TGA AAA TGA CTG AAT ATA AAC TT-3' SEQ ID NO: 21) and Reverse (5'-GAT CAT ATT CGT CCA CAA AAT GA-3'). The results from PCR using Dynabeads with immobilized TagTaq fusion protein were compared with free (i.e. pre-heat eluted) TagTaq fusion protein (94° C. for 5 minutes, supernatant transferred to PCR mix) and AmpliTaq (Perkin Elmer, Norwalk, Conn., USA). PCR reactions' mixtures contained 1x PCR buffer II (Perkin Elmer, Norwalk, Conn., USA), 2.5 mM MgCl$_2$, 200 µM dNTP's, 1 µM primers and 25 ng human genomic DNA as template in a total volume of 30 µl. The reaction mixtures were prepared at room temperature. The PCR amplifications were performed on a PCR 9600 (Perkin Elmer, Norwalk, Conn., USA). The PCR program was: 94° C. for 2 min followed by 34 cycles of (94° C., 30 s, 55° C., 30 s, 72° C., 45 s) and 72° C. for 5 min. The PCR products were analyzed by 3% agarose (NuSieve GTG, FMC, Rockland, Maine, USA) gel electrophoresis and stained with ethidium bromide.

The above method describes the methodology used to investigate the performance of immobilized TagTaq in full multiple-cycle PCR amplifications (FIG. 11). For comparison, a commercially available Taq DNA polymerase was used in a standard protocol (FIG. 11, lane 7) and in a conventional hot start procedure (FIG. 11, lane 8). Analysis of the resulting PCR products by agarose gel electrophoresis shows that for both the immobilized (lanes 1 to 3) and free (pre-heat released, lanes 4 to 6) TagTaq polymerase, the expected PCR product is achieved. However, for the amplification of this fragment, both the use of free TagTaq or a commercial Taq DNA polymerase results in the formation of artefactual primer-dimer products (lanes 4 to 6 and lane 7), which also reduces the product yield. In contrast using either a conventional hot start procedure (lane 8) or immobilized TagTaq polymerase (lanes 1 to 3), high yields of essentially pure, full-length PCR products free from primer-dimers are obtained.

EXAMPLE 3

Immobilization of Enzymes by Different Heat-Sensitive Linkages

The immobilization of different enzymes through different heat-sensitive linkages was performed to investigate their applicability to hot-start PCR.

The following immobilized enzymes were investigated:

BBΔTaq-HSA-DB—comprising BBΔTaq (an N-terminally truncated form of Taq-polymerase, fused to HSA (human serum albumin) binding domain of Streptococcal protein G, as in Example 1) immobilized on HSA-coated Dynabeads.

ABP-Taq-HSA-DB—comprising ABP-Taq (full length Taq-polymerase, fused to HSA-binding domain of Streptococcal protein G) immobilized on HSA-coated Dynabeads.

Aff2Taq-HSA-DB—comprising Aff2Taq (the same full length Taq-polymerase as ABP-Taq, but fused to a tri-partite handle instead of the HSA-binding domain as in Example 2 consisting of a HSA-binding domain, a His6-tag and a sequence leading to biotinylation in vivo in *E. coli*) immobilized on HSA-coated Dynabeads. Aff2Taq-streptavidin-DB—comprising Aff2Taq (as above) immobilized on streptavidin-coated Dynabeads.

Aff2Taq-anti-biotin-RAM-DB—comprising Aff2Taq (as above) immobilized on RAM IgG1-Dynabeads (beads coated with monoclonal antibodies to biotin (Boehringer Mannheim)).

Aff2Taq-TaqStart-antibody-RAM-DB—comprising Aff2Taq (as above) immobilized on RAM IgG2b-Dynabeads (beads coated with "TaqStart antibody" (Clontech), which is a monoclonal antibody to Taq-polymerase).

AmpliTaq-TaqStart antibody-RAM-DB—comprising AmpliTaq (purchased from PerkinElmer) immobilised on RAM IgG2b-Dynabeads (beads coated with TaqStart-antibodies as above).

The coating of RAM IgG-Dynabeads with the commercially available antibodies (to biotin or Taq polymerase) was performed by incubating 2 µg of antibodies per mg of RAM IgG-Dynabeads in 500 µl PBS for 1 hr at room temperature.

Coating of the different kinds of Dynabeads with the different Taqenzymes was performed by incubating 10–15 µg of enzyme with 5mg Dynabeads in 1 x storage buffer (20 mM TrisHCl pH 8, 100 mM KCl, 0.1 mM EDTA, 1 mM DTT, 0.5% Tween20, 0.5% NP40) for 1 hr at room temperature.

PCR was performed using kRAS primers as described in Example 2.

All the immobilised enzymes show hot-start effect in PCR with regard to preventing primer-dimer formation (FIG. 12). Only the positive control (lane 8), in which the PCR enzyme was not inactivated at the onset of PCR showed the production of primer dimers. This experiment illustrates the utility of a number of different methods of linking amplification enzymes to solid supports for use in hot start amplification reactions.

What is claimed is:

1. A reversibly inactivated enzyme or a fragment thereof having catalytic activity of the enzyme, wherein the enzyme or fragment is in the form of a fusion protein that is attached to an immobilizing moiety via a pair of affinity binding partners, wherein the enzyme or fragment is essentially inactive when the fusion protein is attached to the immobilizing moiety and is activated by release of the fusion protein from the immobilizing moiety, wherein the enzyme is selected from the group consisting of DNA polymerases, DNA ligases, reverse transcriptases, and RNA polymerases, and wherein one partner of the pair of affinity binding partners is attached to or is inherently part of the immobilizing moiety, and the other partner of the pair of affinity binding partners is attached to or is inherently part of the fusion protein.

2. The reversibly activated enzyme or catalytic fragment of claim 1, wherein the immobilizing moiety comprises a magnetic particle.

3. A kit for use in a PCR amplification technique, comprising:
   a) a reversibly inactivated thermostable DNA polymerase, wherein the polymerase is in the form of a fusion protein that is bound to an immobilizing moiety via a pair of affinity binding partners, wherein binding of the fusion protein to the immobilizing moiety reversibly inactivates the polymerase, and release of the fusion protein from the immobilizing moiety activates the polymerase, and wherein one partner of the pair of affinity binding partners is attached to or is inherently part of the immobilizing moiety, and the other partner of the pair of affinity binding partners is attached to or is inherently part of the fusion protein; and
   b) a pair of primers which hybridize to opposite strands of a target DNA.

4. A kit for use in an LCR amplification technique, comprising:
   a) a reversibly inactivated thermostable DNA ligase, wherein the ligase is in the form of a fusion protein that is bound to an immobilizing moiety via a pair of affinity binding partners, wherein binding of the fusion protein to the immobilizing moiety reversibly inactivates the ligase, and release of the fusion protein from the immobilizing moiety activates the ligase, and wherein one partner of the pair of affinity binding partners is attached to or is inherently part of the immobilizing moiety, and the other partner of the pair of affinity binding partners is attached to or is inherently part of the fusion protein; and
   b) two pairs of primers, wherein the individual primers of one of the pairs hybridize to adjacent stretches in one strand of a target DNA, and the individual primers of the other pair hybridize to the opposite strand of the target DNA in a region opposite said adjacent stretches.

5. A kit for use in a 3SR amplification technique, comprising:
   a) a reversibly inactivated, thermostable reverse transcriptase or RNA polymerase, wherein the transcriptase or RNA polymerase is in the form of a fusion protein that is bound to an immobilizing moiety via a pair of affinity binding partners, wherein binding of the fusion protein to the immobilizing moiety reversibly inactivates the transcriptase or polymerase, and release of the fusion protein from the immobilized moiety activates the transcriptase or polymerase, and wherein one partner of the pair of affinity binding partners is attached to or is inherently part of the immobilizing moiety, and the other partner of the pair of affinity binding partners is attached to or is inherently part of the fusion protein; and
   b) a pair of primers which hybridize to opposite strands of a target DNA or RNA and which each have a transcriptase or polymerase binding site.

6. A kit for use in RT-PCR amplification techniques, comprising:
   a) a reversibly inactivated thermostable reverse transcriptase, wherein the transcriptase is in the form of a fusion protein that is attached to an immobilizing moiety via a pair of affinity binding partners, wherein binding of the fusion protein to the immobilizing moiety reversibly inactivates the reverse transcriptase, and release of the fusion protein from the immobilizing moiety activates the transcriptase, and wherein one partner of the pair of affinity binding partners is attached to or is inherently part of the immobilizing moiety, and the other partner of the pair of affinity binding partners is attached to or is inherently part of the fusion protein;
   b) a RT primer which binds to a target RNA for generating a complementary DNA (cDNA); and
   c) a pair of PCR primers which hybridize to opposite strands of a double-stranded DNA, one strand of which is the cDNA.

7. A kit for use in Q-beta amplification techniques, comprising:
   a) reversibly inactivated a thermostable RNA-directed RNA polymerase, wherein the polymerase is in the form of a fusion protein that is bound to an immobilizing moiety via a pair of affinity binding partners, wherein binding of the fusion protein to the immobilizing moiety reversibly inactivates the polymerase, and release of the fusion protein from the immobilizing moiety activates the polymerase, and wherein one partner of the pair of affinity binding partners is attached to or is inherently part of the immobilizing moiety, and the other partner of the pair of affinity binding partners is attached to or is inherently part of the fusion protein; and
   b) an RNA probe with a 5'-MDV-1 structure, the RNA probe being immobilized or permitting immobilization.

8. A method of activating a reversibly inactivated enzyme or a fragment thereof having catalytic activity of the enzyme, wherein the enzyme or fragment is in the form of a fusion protein and is inactivated by attachment of the fusion protein to an immobilizing moiety via a pair of affinity binding partners and is activated by release of the fusion protein from the immobilizing moiety, said method comprising releasing the fusion protein from said immobilizing moiety, wherein the enzyme is selected from the group consisting of DNA polymerases, DNA ligases, reverse transcriptases, and RNA polymerases, and wherein one partner of the pair of affinity binding partners is attached to or is inherently part of the immobilizing moiety, and the other partner of the pair of affinity binding partners is attached to or is inherently part of the fusion protein.

9. A method as claimed in claim 8 wherein said enzyme or fragment is thermostable.

10. A method as claimed in claim 9 wherein said enzyme is DNA polymerase from *Thermus thermophilus* or *Thermus aquaticus*.

11. A method as claimed in claim 8 wherein said fusion protein is bound to the immobilizing moiety via a heat-labile linkage.

12. A method as claimed in claim 8, wherein one partner of said pair of affinity binding partners is inherently part of said fusion protein.

13. A method as claimed in claim 8, wherein said pair of affinity binding partners is (a) protein A or a part thereof having the function of protein A, and (b) immunoglobulin G (IgG) or a part thereof having the function of IgG.

14. A method as claimed in claim 8, wherein said pair of affinity binding partners is (a) protein G or a part thereof having the function of protein G, and (b) human serum albumin (HSA) or a part thereof having the function of HSA.

15. A method as claimed in claim 12 wherein said one partner is an epitope of said enzyme or fragment, or of a moiety appended to said enzyme or fragment, and the other binding partner is an antibody which specifically recognizes said epitope.

16. A method as claimed in claim 8 wherein said immobilizing moiety comprises a magnetic particle.

17. A method of amplifying a nucleic acid, the method comprising:
   providing a reversibly inactivated enzyme or a fragment thereof having catalytic activity of the enzyme, wherein said enzyme or fragment is in the form of a fusion protein that is bound to an immobilizing moiety via a pair of affinity binding partners, wherein binding of the fusion protein to the immobilizing moiety via the pair of affinity binding partners reversibly inactivates the enzyme or fragment and release of the fusion protein from the immobilizing moiety activates the enzyme or fragment, wherein the enzyme or fragment is selected from the group consisting of DNA polymerases, DNA ligases, reverse transcriptases, and RNA polymerases, and wherein one partner of the pair of affinity binding partners is attached to or is inherently part of the immobilizing moiety, and the other partner of the pair of affinity binding partners is attached to or in inherently part of the fusion protein;
   contacting a sample containing the nucleic acid with the enzyme or fragment; and
   releasing the fusion protein from the immobilizing moiety, thereby activating the enzyme or fragment and starting a first cycle of an amplification reaction.

18. A method as claimed in claim 17, wherein the amplification reaction is polymerase chain reaction (PCR).

19. A method as claimed in claim 17 wherein said amplification reaction is selected from the group consisting of Ligase chain reaction (LCR), Self-sustained Sequence Replication (3SR), Reverse transcriptase PCR (RT-PCR), Q-beta replicase amplification reaction, and nucleic acid sequence-based amplification (NASBA).

* * * * *

SEQUENCE LISTING

<160> NUMBER OF SEQ ID NOS: 23

<210> SEQ ID NO 1
<211> LENGTH: 32
<212> TYPE: DNA
<213> ORGANISM: Thermus aquaticus

<400> SEQUENCE: 1
gggaattcca tggacgatct gaagctctcc tg                                    32

<210> SEQ ID NO 2
<211> LENGTH: 32
<212> TYPE: DNA
<213> ORGANISM: Thermus aquaticus

<400> SEQUENCE: 2
ccccaagctt ctgcaggatc ttctccacga tg                                    32

<210> SEQ ID NO 3
<211> LENGTH: 20
<212> TYPE: DNA
<213> ORGANISM: Thermus aquaticus

<400> SEQUENCE: 3
gaagatcctg cagtaccggg                                                  20

<210> SEQ ID NO 4
<211> LENGTH: 26
<212> TYPE: DNA
<213> ORGANISM: Thermus aquaticus

<400> SEQUENCE: 4
gggtcgacct ccttggcgga gagcca                                           26

<210> SEQ ID NO 5
<211> LENGTH: 15
<212> TYPE: DNA
<213> ORGANISM: Thermus aquaticus

<400> SEQUENCE: 5
gtcgactaac tgcag                                                       15

<210> SEQ ID NO 6
<211> LENGTH: 27
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: (1)...(1)
<223> OTHER INFORMATION: n = modified nucleotide (fluorescein-labeled c)

<400> SEQUENCE: 6
nagtcacgac gttgtaaaac ggccagt                                          27

<210> SEQ ID NO 7
<211> LENGTH: 37
<212> TYPE: DNA
<213> ORGANISM: Artificial Sequence
<220> FEATURE:
<223> OTHER INFORMATION: Synthetically generated primer

<400> SEQUENCE: 7

```
ccctgatcac catgggcgca acacgatgaa gccgtag                             37
```

<210> SEQ ID NO 8
<211> LENGTH: 51
<212> TYPE: DNA
<213> ORGANISM: Artificial Sequence
<220> FEATURE:
<223> OTHER INFORMATION: Synthetically generated primer

<400> SEQUENCE: 8

```
ggggatcca tgtagtgagc gaaggtacca ttcgcgtcta ctttcggcgc c              51
```

<210> SEQ ID NO 9
<211> LENGTH: 36
<212> TYPE: DNA
<213> ORGANISM: Streptococcus

<400> SEQUENCE: 9

```
ccgaattcgc tagcttagct gaagctaaag tcttag                              36
```

<210> SEQ ID NO 10
<211> LENGTH: 32
<212> TYPE: DNA
<213> ORGANISM: Streptococcus

<400> SEQUENCE: 10

```
ccggtaccag gtaatgcagc taaaatttca tc                                  32
```

<210> SEQ ID NO 11
<211> LENGTH: 27
<212> TYPE: DNA
<213> ORGANISM: Coxsackievirus

<400> SEQUENCE: 11

```
aatttggaag ctctgttcca gggtccg                                        27
```

<210> SEQ ID NO 12
<211> LENGTH: 27
<212> TYPE: DNA
<213> ORGANISM: Coxsackievirus

<400> SEQUENCE: 12

```
aattcggacc ctggaacaga gcttcca                                        27
```

<210> SEQ ID NO 13
<211> LENGTH: 63
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: (1)...(1)
<223> OTHER INFORMATION: n = modified nucleotide (biotin-conjugated c)

<400> SEQUENCE: 13

```
ntagtagcct gcgccagatc ctggacagcc agaaaatsga atggcgcagc aacgctggtg    60
gtg                                                                  63
```

<210> SEQ ID NO 14
<211> LENGTH: 63
<212> TYPE: DNA
<213> ORGANISM: Artificial Sequence
<220> FEATURE:

```
<223> OTHER INFORMATION: Synthetically generated primer
<220> FEATURE:
<221> NAME/KEY: misc_feature
<222> LOCATION: (1)...(1)
<223> OTHER INFORMATION: n = modified nucleotide (biotin-conjugated c)

<400> SEQUENCE: 14
ntagcaccac cagcgttgct gcgccattcs attttctggc tgtccaggat ctggcgcagg      60
caa                                                                   63

<210> SEQ ID NO 15
<211> LENGTH: 30
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: (1)...(1)
<223> OTHER INFORMATION: n = modified nucleotide (his-conjugated c)

<400> SEQUENCE: 15
ntagtcacca ccaccaccac cacggtggtg                                       30

<210> SEQ ID NO 16
<211> LENGTH: 30
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: (1)...(1)
<223> OTHER INFORMATION: n = modified nucleotide (his-conjugated c)

<400> SEQUENCE: 16
ntagcaccac cgtggtggtg gtggtggtga                                       30

<210> SEQ ID NO 17
<211> LENGTH: 35
<212> TYPE: DNA
<213> ORGANISM: Thermus aquaticus

<400> SEQUENCE: 17
cacgcgtcga cctccttggc ggagagccag tcctc                                 35

<210> SEQ ID NO 18
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 18
tcgactaact gcaggcatgc a                                                21

<210> SEQ ID NO 19
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 19
agcttgcatg cctgcagtta g                                                21
```

```
<210> SEQ ID NO 20
<211> LENGTH: 27
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: (1)...(1)
<223> OTHER INFORMATION: n = modified nucleotide (fluorescein-labeled c)

<400> SEQUENCE: 20
nagtcacgac gttgtaaaac ggccagt                                              27

<210> SEQ ID NO 21
<211> LENGTH: 23
<212> TYPE: DNA
<213> ORGANISM: Homo sapiens

<400> SEQUENCE: 21
tgaaaatgac tgaatataaa ctt                                                  23

<210> SEQ ID NO 22
<211> LENGTH: 23
<212> TYPE: DNA
<213> ORGANISM: Homo sapiens

<400> SEQUENCE: 22
gatcatattc gtccacaaaa tga                                                  23

<210> SEQ ID NO 23
<211> LENGTH: 7
<212> TYPE: PRT
<213> ORGANISM: Coxsackievirus

<400> SEQUENCE: 23

Glu Ala Leu Phe Gln Gly Pro
  1               5
```